(12) United States Patent
Jutras

(10) Patent No.: US 9,999,558 B2
(45) Date of Patent: *Jun. 19, 2018

(54) PIECE OF FURNITURE, SUCH AS AN ADJUSTABLE BED, HAVING AN ADJUSTABLE PLATFORM

(71) Applicant: USINE ROTEC INC., Baie-du-Febvre (CA)

(72) Inventor: Robert Jutras, Baie-du-Febvre (CA)

(73) Assignee: USINE ROTEC INC., Baie-du-Febvre (CA)

(*) Notice: Subject to any disclaimer, the term of this patent is extended or adjusted under 35 U.S.C. 154(b) by 0 days. days.

This patent is subject to a terminal disclaimer.

(21) Appl. No.: 15/471,388

(22) Filed: Mar. 28, 2017

(65) Prior Publication Data

US 2017/0258655 A1 Sep. 14, 2017

Related U.S. Application Data

(63) Continuation-in-part of application No. 15/064,025, filed on Mar. 8, 2016, now Pat. No. 9,757,292, which
(Continued)

(51) Int. Cl.
*A61G 7/012* (2006.01)
*A61G 7/005* (2006.01)
*A47C 19/04* (2006.01)

(52) U.S. Cl.
CPC ............ *A61G 7/012* (2013.01); *A47C 19/045* (2013.01); *A61G 7/005* (2013.01)

(58) Field of Classification Search
CPC ........ A61G 7/012; A61G 7/005; A61G 7/015; A47C 19/045
See application file for complete search history.

(56) References Cited

U.S. PATENT DOCUMENTS 2,527,111 A 10/1950 Widrich
3,644,944 A 2/1972 Bourgraf et al.
(Continued)

FOREIGN PATENT DOCUMENTS

DE 19915431 10/2000
EP 2189140 5/2010
(Continued)

OTHER PUBLICATIONS

European Supplementary Search Report, European Patent Office, European Patent Application No. 12770576.2, dated Sep. 19, 2014.
(Continued)

*Primary Examiner* — Eric J Kurilla
(74) *Attorney, Agent, or Firm* — Norton Rose Fulbright Canada LLP

(57) ABSTRACT

An adjustable bed having a mattress support platform and a fixed frame base with wheels. A lift mechanism interconnects the mattress support platform and the fixed frame base to displace the mattress support platform between a fully collapsed position and a fully elevated position. The lift mechanism includes leg members pivotally connected with the fixed frame base and with the mattress support platform. A force multiplying actuating linkage interconnects an actuator and the fixed frame base. The actuating linkage includes a driving link and an intermediate link. The driving link has a first end pivotally mounted to the fixed frame base and a second end pivotally connected to the actuator. The intermediate link is pivotally connected to the driving link, and is pivotally engaged with one of the leg members and a stabilizing link. The stabilizing link interconnects one of the leg members and the fixed frame base.

20 Claims, 16 Drawing Sheets

Related U.S. Application Data is a continuation of application No. 14/111,317, filed as application No. PCT/CA2012/050232 on Apr. 11, 2012, now Pat. No. 9,314,385.

(60) Provisional application No. 61/473,968, filed on Apr. 11, 2011.

(56) References Cited

U.S. PATENT DOCUMENTS

| | | |
|---|---|---|
| 3,802,002 A | 4/1974 | Jonas |
| 4,718,355 A | 1/1988 | Houghton |
| 5,687,437 A | 11/1997 | Goldsmith |
| 5,720,059 A | 2/1998 | Allevato |
| 6,161,236 A | 12/2000 | Carroll |
| 6,289,536 B1 | 9/2001 | Betson |
| 6,351,861 B1 | 3/2002 | Shows |
| 6,405,393 B2 | 6/2002 | Megown |
| 6,473,922 B1 | 11/2002 | Sommerfeld et al. |
| 6,578,216 B1 | 6/2003 | Aarestad |
| 6,920,656 B2 | 7/2005 | Roussy |
| 7,013,510 B1 | 3/2006 | Johnson |
| 7,185,377 B2 | 3/2007 | Roussy |
| 7,334,277 B2 | 2/2008 | Johnson |
| 7,509,697 B2 | 3/2009 | Dorenbeck |
| 7,631,379 B2 | 12/2009 | Lindner |
| 7,774,876 B2 | 8/2010 | Brown et al. |
| 7,802,331 B2 | 9/2010 | Brown et al. |
| 9,107,781 B1 | 8/2015 | Edgerton |
| 2001/0047547 A1 | 12/2001 | Paul |
| 2002/0144348 A1 | 10/2002 | Ganance |
| 2003/0172459 A1 | 9/2003 | Roussy |
| 2006/0021143 A1 | 2/2006 | Lemire |
| 2006/0085914 A1 | 4/2006 | Peterson |
| 2007/0226907 A1 | 10/2007 | Dorenbeck |
| 2007/0234477 A1 | 10/2007 | Dorenbeck |
| 2009/0094747 A1 | 4/2009 | Bly |
| 2009/0172883 A1 | 7/2009 | Benedict |
| 2009/0282616 A1 | 11/2009 | Carr |
| 2011/0113556 A1 | 5/2011 | Roussy |
| 2013/0219382 A1 | 8/2013 | Parsons |
| 2014/0041120 A1 | 2/2014 | Li |
| 2014/0075674 A1 | 3/2014 | Chun |
| 2015/0033472 A1 | 2/2015 | Li |
| 2015/0135431 A1 | 5/2015 | Dindas |
| 2015/0135439 A1 | 5/2015 | Sammons |
| 2016/0184152 A1 | 6/2016 | Jutras |

FOREIGN PATENT DOCUMENTS

| | | |
|---|---|---|
| WO | 2004080363 | 9/2004 |
| WO | 2007069912 | 6/2007 |

OTHER PUBLICATIONS

International Report on Patentability, International Preliminary Examining Authority (CIPO), PCT Application No. PCT/CA2012/050232, dated Aug. 16, 2013.

International Search Report and Written Opinion, International Searching Authority (CIPO), PCT Application No. PCT/CA2012/050232, dated Jul. 5, 2012.

Requisito 1 (Office Action), Instituto Mexicano de la Propiedad Industrial, Mexican Patent Application No. 7MX/a/2013/011934, dated Sep. 11, 2015.

Office Action, Canadian Intellectual Property Office, Canadian Patent Application No. 2,831,004, dated Mar. 13, 2015.

Office Action, Canadian Intellectual Property Office, Canadian Patent Application No. 2,831,004, dated Apr. 23, 2015.

Office Action, IP Australia, Australian Patent Application No. 2012243409, dated Oct. 19, 2015.

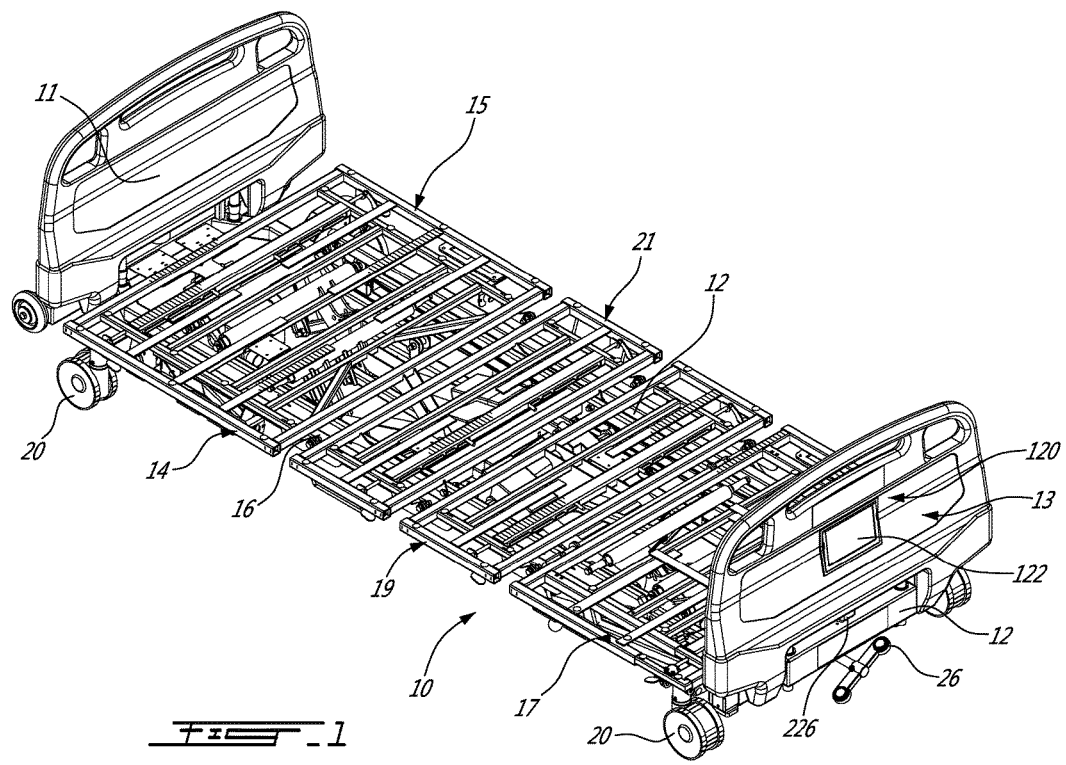

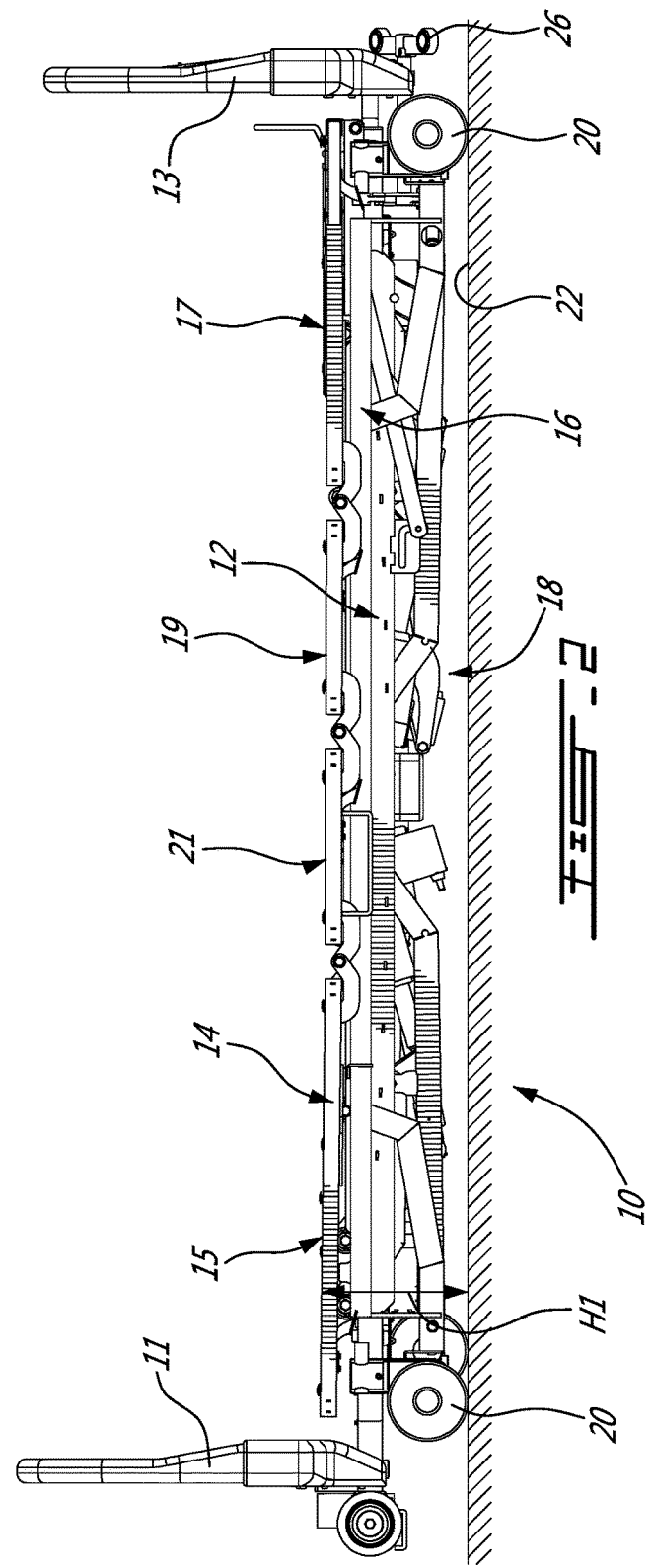

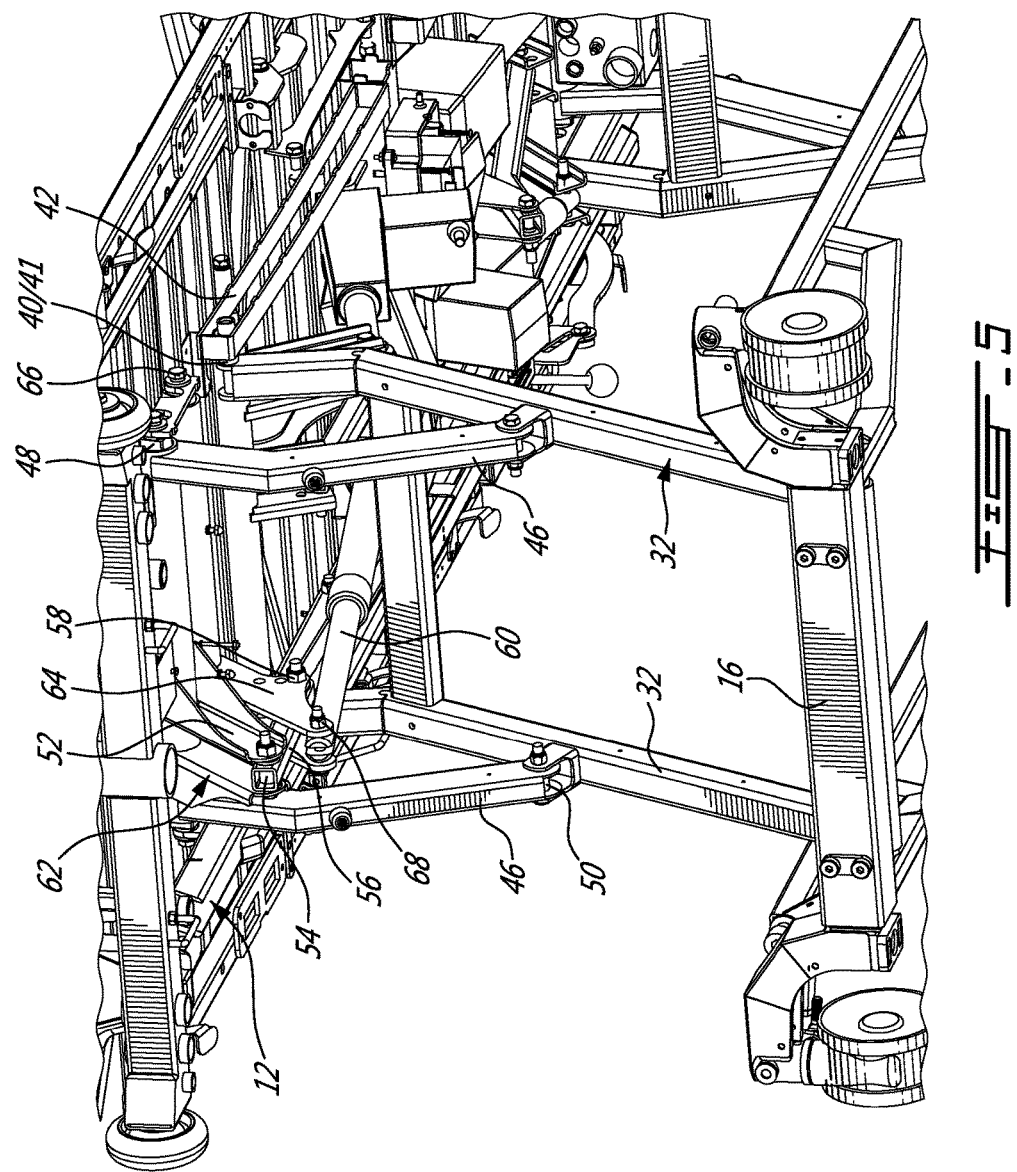

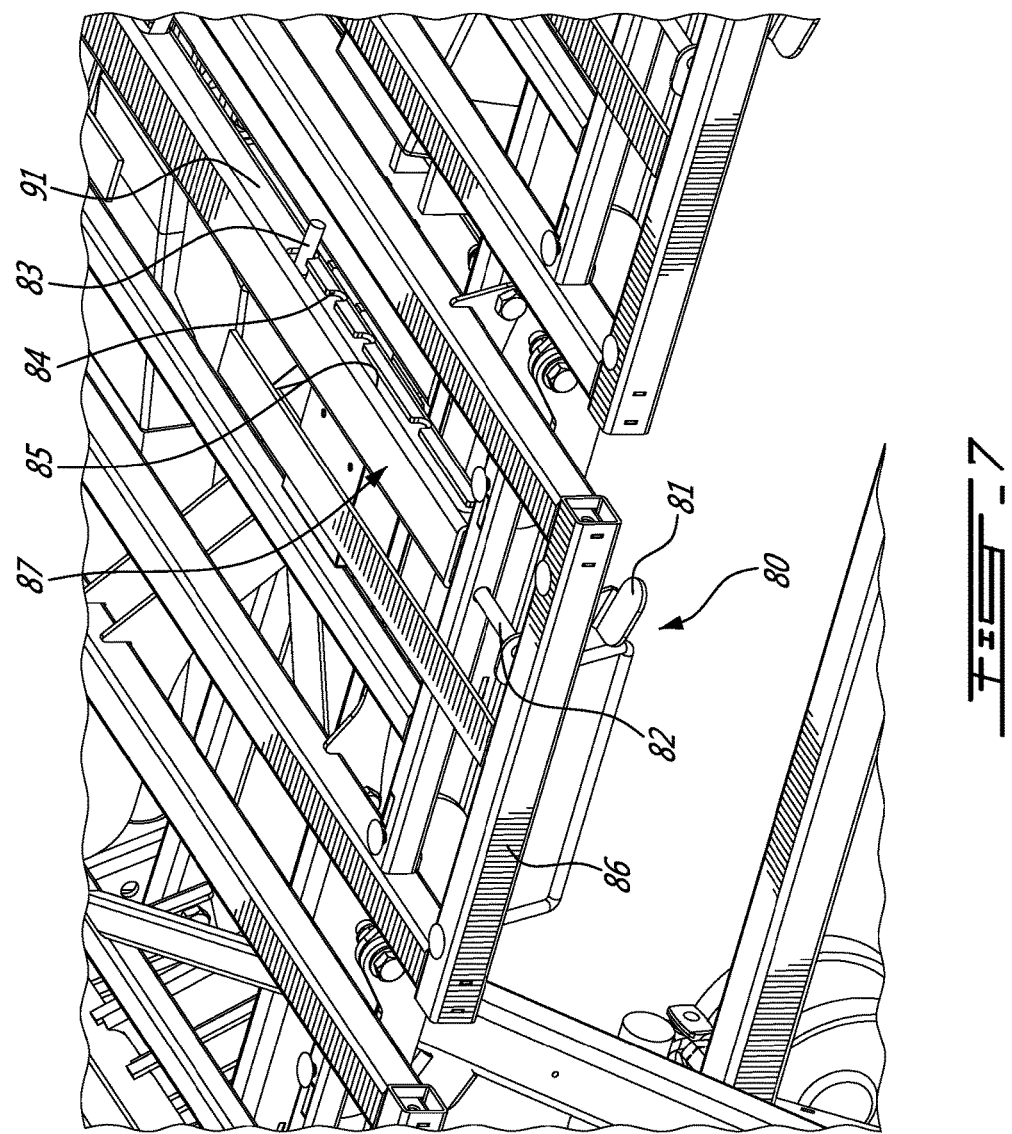

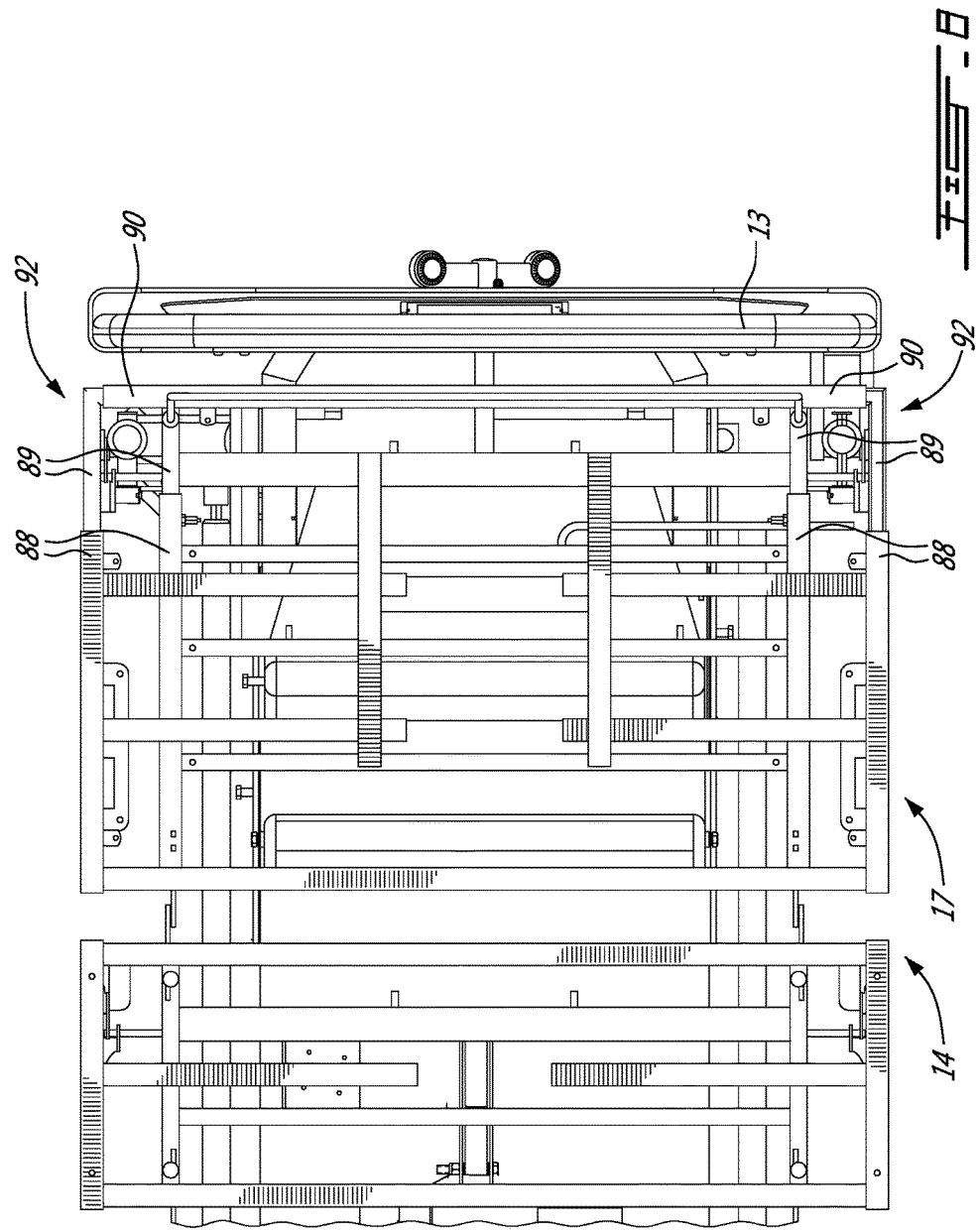

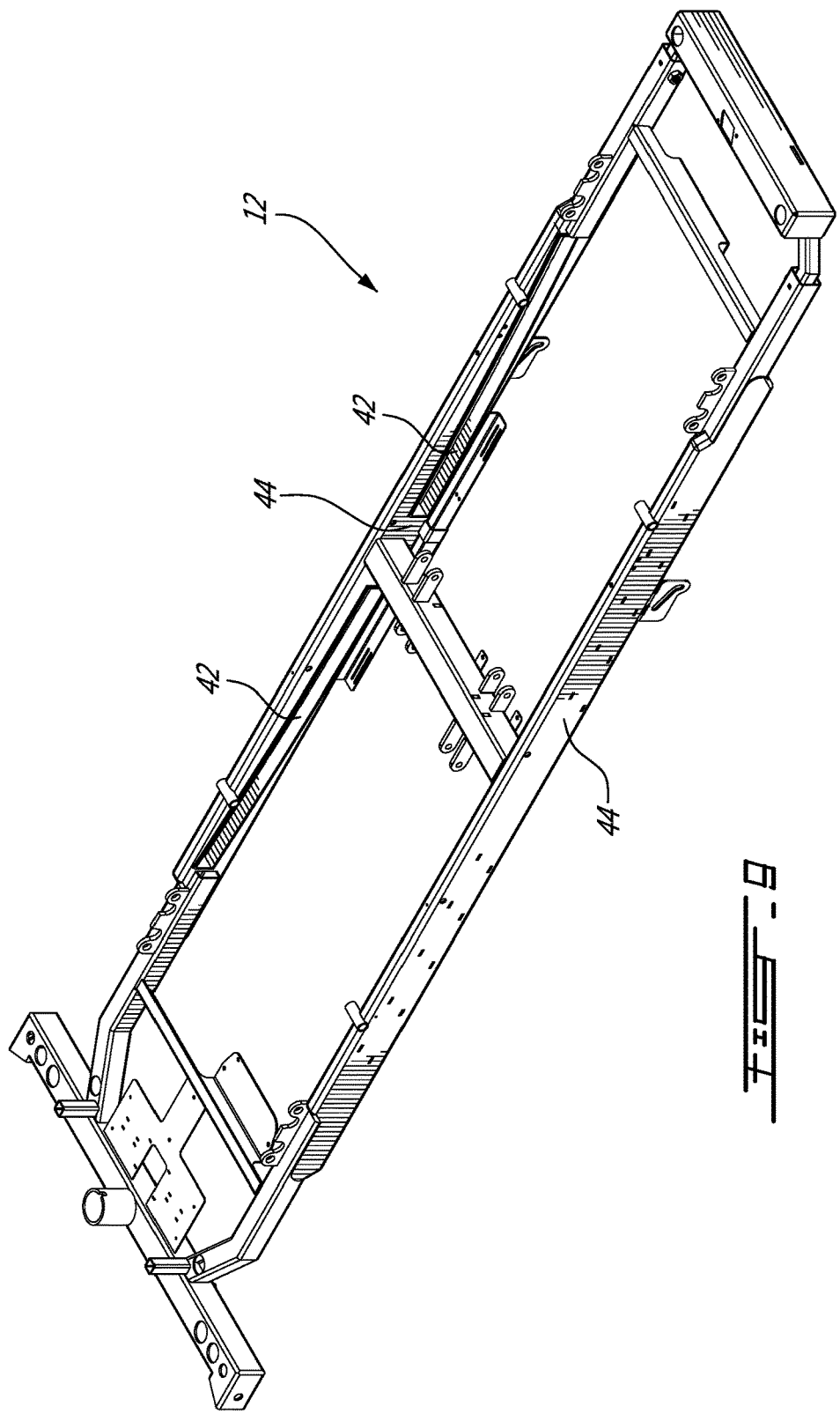

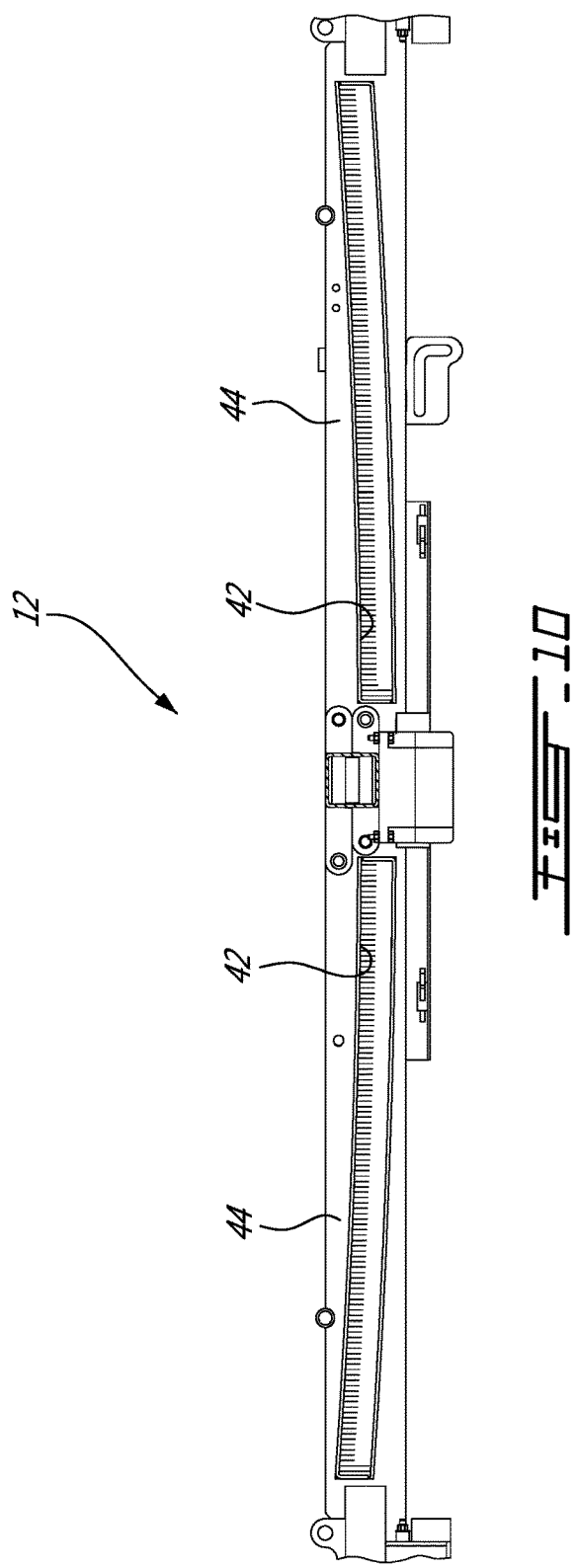

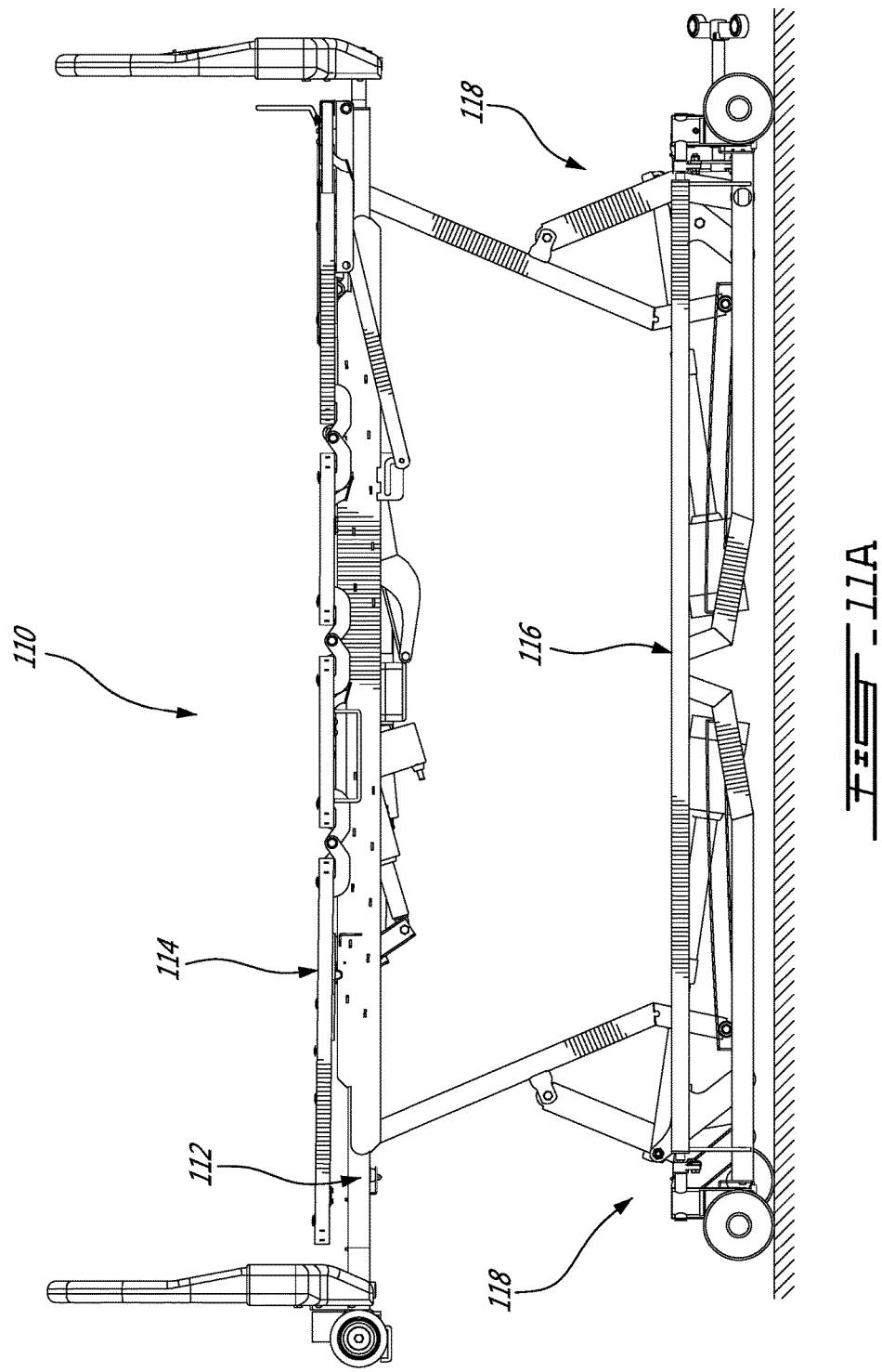

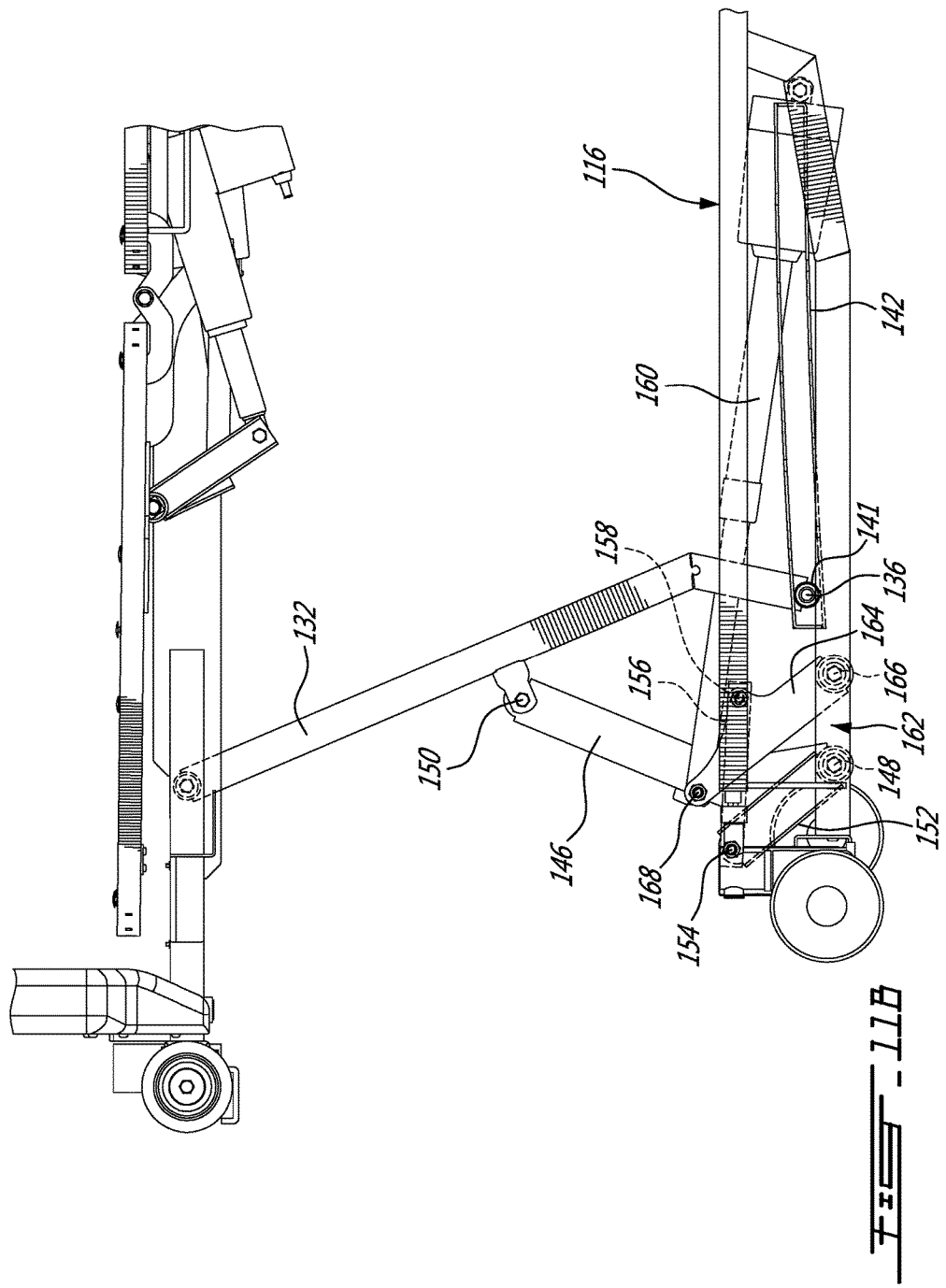

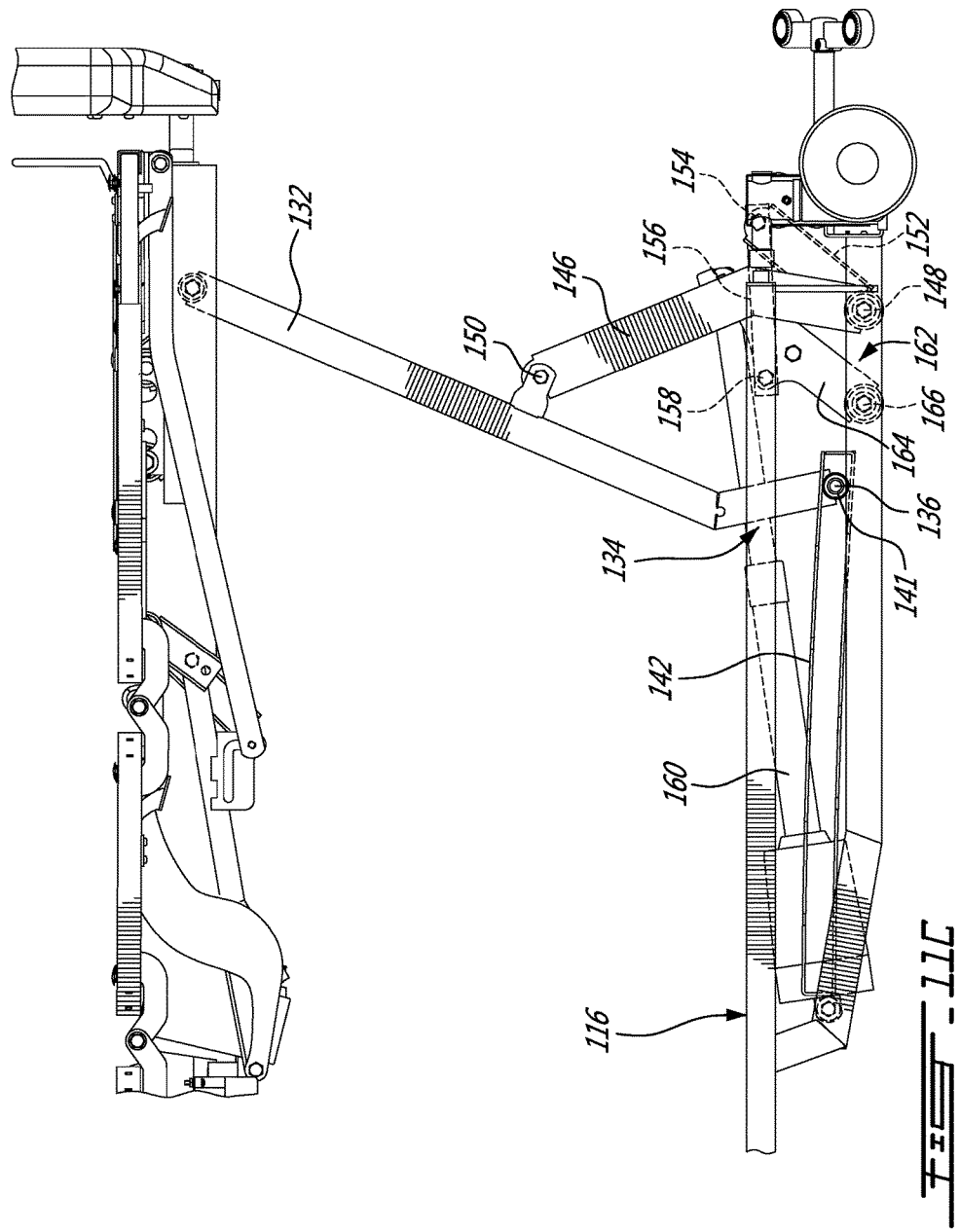

PIECE OF FURNITURE, SUCH AS AN ADJUSTABLE BED, HAVING AN ADJUSTABLE PLATFORM

CROSS-REFERENCE TO RELATED APPLICATIONS

The present application is a continuation-in-part of U.S. patent application Ser. No. 15/064,025 filed Mar. 8, 2016, which is a continuation of U.S. patent application Ser. No. 14/111,317 filed Oct. 11, 2013, now issued U.S. Pat. No. 9,314,385, which is a 371 of PCT/CA2012/50232 filed Apr. 11, 2012 that claims priority benefit of U.S. Patent Application No. 61/473,968 filed Apr. 11, 2011, the entire contents of each which is incorporated herein by reference.

TECHNICAL FIELD

The present disclosure relates generally to a piece of furniture, such as an adjustable bed, table or chair, which includes a lift mechanism for an adjustable platform, and more particular to an adjustable bed having a high lift capacity while minimizing the elevation of the bed when fully lowered.

BACKGROUND

Adjustable beds are well known, and are used in a variety of applications including for medical or domestic use. Such adjustable beds are often used by people having limited mobility, be it as a result of being obese, having a medical condition, or otherwise. Adjustable beds are often used in hospitals and other medical care facilities, however a growing number of obese and other mobility challenged people are using adjustable beds domestically to improve their quality of life. Adjustable beds are typically articulated in at least one location, and enable the orientation and vertical elevation of the sleep surface to be modified as required.

"Low-profile" adjustable beds, namely beds which allow the sleeping surface to be positioned very close to the ground when the bed is disposed in its fully collapsed or fully lowered position, are becoming increasing popular. There are several advantages associated with being able to collapse a bed to such a low-profile position, the primary among which is that they make the process of getting onto and off the bed much easier for the user/patient. Another advantage of low-profile beds, particularly useful for hospital patients which are at risk of falling out of a hospital bed, is that they enable the sleeping surface to be positioned as close to the ground as possible.

However, these low-profile beds must still be able to be adjusted such that they can be raised to a much higher position so that medical staff have comfortable access to the patient. Due to the mechanisms required to permit the movement of the bed and the motors required to actuate such mechanisms, such known low-profile beds do not normally allow a fully-collapsed position of less than about 8 inches above the ground surface. Additionally, another disadvantage of known low-profile beds is that the typical configurations of the lifting mechanisms of a very low-profile bed typically place the actuators for raising and lowering the bed at a very shallow angle when the bed is in the fully lowered/collapsed position. Accordingly the actuators, which are already limited somewhat in lifting capacity by their small size required for them to fit within the tight space envelope of such a low-profile bed structure, can only produce a small vertical force component due to the relatively shallow angle at which the actuator is positioned beneath the bed. As such, this small vertical force component can significantly limit, if not completely prevent, the ability to lift the bed and patient.

In the past, these drawbacks have limited the minimum height of mechanically actuated adjustable beds as well as their maximum lift capacity (ex: maximum weight of patient). For example, for the reasons set out above, most existing low-profile beds which permit a minimum vertical height (i.e. in the fully-lowered position) of 8 inches or less, have a maximum lift capacity of 500 lbs. Accordingly, these low-profile beds become unsuitable for obese patients/users weighing more than 500 lbs. As a means for comparison, adjustable beds of the type specifically designed for obese patients typically have a maximum lift capacity of 1000 lbs, however these obese-specific beds cannot be lowered into a low profile position. Attempts to design a bed which reaches a compromise between lift capacity and minimum fully-lowered height have been attempted, however such beds typically only permit a height adjustment range of 9.5 to 29 inches at a maximum load of 850 lbs (i.e. they only permit a minimum elevation of 9.5 inches when disposed in the fully-lowered position, and can only support a patient of less than 850 lbs). Thus, such beds either cannot be collapsed into a real low-profile position (ex: less than 9.5 inches) due to the larger actuators and mechanism geometry which permit a higher lift capacity, or have limited lift capacity.

Attempts to address the above-mentioned issues have been made. U.S. Pat. No. 6,473,922 issued Nov. 5, 2002 to Sommerfeld et al. discloses, for example, an articulated bed which attempt to minimize the amount of force required to raise the bed from its lowered position. However, several disadvantages exist with this articulated bed structure. The bed taught by Sommerfeld includes a main frame, on which the sleep surface platform is mounted, and which is supported by a pair of pivoting legs. The legs are supported and actuated by stabilizers, and have wheels on the outer free ends thereof. Accordingly, in order for the sleep surface to be vertically raised or lowered, the pivoting legs must swing through their travel arc, as shown in FIG. 2 for example. This results in vertical displacement of the entire bed structure. As can be seen in FIG. 2 of Sommerfeld, for example, if the longitudinal position of the end of a first one of the pivoting legs (such as the one closest to the headboard for example) is kept stationary, then actuating the bed to raise or lower the sleep surface will cause the opposite second leg to move longitudinally outward as the leg pivots through its radius of travel. This accordingly causes a longitudinal displacement of the entire bed, in this case in a direction towards the foot of the bed. Clearly, such lateral translation of the entire bed during height adjustment is undesirable. Other disadvantages with the bed described in U.S. Pat. No. 6,473,922 also exist. For example, this configuration requires the bed to be moved into its fully collapsed/lowered position, as shown in FIG. 1 for example, before the entire bed can be displaced on the floor. Once in the fully lowered position, the caster wheels mounted on the main frame engage the floor, thereby permitting displacement of the bed as needed, for example to move the bed from one hospital room to another. When the bed is in an extended position, whereby the sleep surface is raised away from the fully collapsed position, the bed is not displaceable. Clearly, this is undesirable, particularly in hospital and other medical applications.

Sommerfeld's articulated bed structure is of the type without a fixed base. Fixed base beds are often preferred because they eliminate any possibility that the bed is laterally displaced (either longitudinally (forward-backward), or laterally (sideways)) during the vertical height adjustment of the sleep surface. However, fixed base bed designs have, in the past, been incompatible with permitting a very low minimum height—i.e. existing fixed base bed designs have not been able to accommodate the desired low-profile minimum height position, because the fixed base alone is often higher than the desired minimum sleep surface height of 8 inches or less, and therefore the overall minimum height of such beds is often over 12 inches in the fully collapsed position. This is considered undesirable for applications in which a low-profile bed is desired or required.

There therefore remains a need for an improved adjustable bed or other adjustable platform, particularly one having a high lift capacity while minimizing the elevation of the bed when fully lowered.

SUMMARY

There is therefore provided an adjustable bed, comprising: a mattress support platform; a fixed frame base having wheels for displacement of the adjustable bed on a floor surface, the fixed frame base at least partially lying in a plane substantially parallel to the floor surface, and the wheels remaining in fixed locations on the fixed frame base regardless of a vertical position of the mattress support platform relative to the fixed frame base; and a lift mechanism interconnecting the mattress support platform and the fixed frame base, the lift mechanism being actuable to displace the mattress support platform between a fully collapsed position and a fully elevated position, the lift mechanism including: two or more leg members each having a first end pivotally connected with the fixed frame base at a first pivot and a second end pivotally connected with the mattress support platform at a second pivot; and an actuating assembly including at least one actuator having a force multiplying actuating linkage interconnecting the actuator and the fixed frame base, the actuator having a first end and a second end, the force multiplying actuating linkage including a driving link and an intermediate link, the driving link having a first end pivotally mounted to the fixed frame base and a second end pivotally connected to the second end of the actuator, and the intermediate link having a first end pivotally connected to the driving link between the first and second ends of the driving link, an opposed second end of the intermediate link being pivotally engaged with one of the leg members and a stabilizing link, the stabilizing link interconnecting one of the leg members and the fixed frame base.

There is further provided an adjustable bed comprising: a main frame having one or more longitudinally extending beams which support a mattress platform; a fixed frame base having wheels for displacement of the fixed frame base on a floor surface, the fixed frame base at least partially lying in a plane substantially parallel to the floor surface, and the wheels remaining in fixed locations on the fixed frame base regardless of a vertical position of the main frame relative to the fixed frame base; and a lift mechanism interconnecting the main frame and the fixed frame base, the lift mechanism supporting the main frame and being actuable to displace the main frame between a fully collapsed position and a fully elevated position relative to the fixed frame base without any longitudinal displacement of the adjustable bed on the floor surface, the lift mechanism including: two or more leg members each having a first end pivotally connected with the fixed frame base at a lower pivot and a second end pivotally connected with the main frame at a movable upper pivot; at least one stabilizer link for each said leg member, the stabilizer link having an upper end pivotally connected with the main frame and a lower end pivotally connected with each said leg member at an intermediate pivot point disposed on the leg member between the first and second ends thereof, the stabilizer link including a torque arm having a remote end disposed a distance away from the upper end of the stabilizer link; and an actuating assembly including at least one actuator having a first end engaged to the main frame, and a force multiplying actuating linkage interconnecting the actuator and the torque arm of the stabilizer link, the actuator having a first end engaged to the main frame and a second end pivotally connected with the force multiplying actuating linkage.

A low-profile bed having a high lift capacity and a low-profile elevation when fully collapsed, while still permitting a large vertical height adjustment and full range of angular adjustments between the articulated sections of the bed, is thereby provided.

In accordance with another aspect of the present disclosure, there is also provided an adjustable bed comprising: a main frame having at least a pair of longitudinally extending, transversely spaced apart, beams which support a mattress platform; a fixed frame base having wheels mounted thereto for displacement of the fixed frame base on a floor surface, the fixed frame base at least partially lying in a plane substantially parallel to the floor surface, and the wheels remaining in fixed locations on the fixed frame base regardless of a vertical position of the main frame relative to the fixed frame base; and a lift mechanism interconnecting the main frame and the fixed frame base, the lift mechanism supporting the main frame and being actuable to displace and position the main frame between a fully collapsed position and a fully elevated position relative to the fixed frame base without any longitudinal displacement of the bed; wherein the main frame, the fixed base and the lift mechanism collapse into a low profile bed configuration in the fully collapsed position, the mattress platform mounted to the main frame being located at a minimum vertical height of at most 9 inches above the floor surface in said low profile bed configuration.

The lift mechanism of the adjustable bed as defined in the preceding paragraph may further include: two or more leg members each having a first end pivotally connected with the fixed frame base at a lower pivot and a second end pivotally connected with the main frame at a movable upper pivot; at least one stabilizer link for each said leg member, the stabilizer link having an upper end pivotally connected with the main frame and a lower end pivotally connected with each said leg member at an intermediate pivot point disposed on the leg member between the first and second ends thereof; and an actuating assembly including at least one actuator for each said leg member and a force multiplying actuating linkage interconnecting the actuator and the stabilizer link, the actuator having a first end engaged to the main frame and a second end pivotally connected with the force multiplying actuating linkage.

The force multiplying actuating linkage of the adjustable bed as defined in the above two paragraphs may further include a driving link and an intermediate link, the driving link having an upper end pivotally mounted to the main frame and a lower end pivotally connected to the second end of the actuator, and the intermediate link having a first end pivotally connected to the driving link between the upper and lower ends thereof and an opposed second end pivotally engaged with the stabilizer link. The stabilizer link of the adjustable bed as defined above may further include a torque arm having a remote end disposed a distance away from the upper end of the stabilizer link, the opposed second end of the intermediate link being pivotally connected with the remote end of the torque arm.

In accordance with another aspect of the present disclosure, there is also provided a piece of furniture having an adjustable platform comprising: a main frame having a support platform mounted thereon; a base having wheels mounted thereto for displacement of the base on a floor surface, the base remaining stationary when the main frame is displaced relative thereto by a lift mechanism interconnecting the main frame and the base; and wherein the lift mechanism supports the main frame and is actuable to displace and position the main frame at any point between a fully collapsed position, wherein the support platform is located at a minimum vertical height above the floor surface, and a fully extended position, wherein the support platform is located at a maximum vertical height above the floor surface, the lift mechanism comprising: two or more leg members each having a first end pivotally connected with the fixed base at a lower pivot and a second end pivotally connected with the main frame at a movable upper pivot, the movable upper pivot of each said leg member being slidingly displaceable within a curvilinear track defined within the longitudinally extending beams of the main frame; at least one stabilizer link for each said leg member, the stabilizer link having an upper end pivotally connected with the main frame and a lower end pivotally connected with each said leg member at an intermediate pivot point disposed on the leg member between the first and second ends thereof; and an actuating assembly including at least one actuator for each said leg member, the actuator having a first end engaged to the main frame and a second end pivotally connected with a force multiplying actuating linkage pivotally interconnecting the actuator and the stabilizer link.

BRIEF DESCRIPTION OF THE DRAWINGS

Reference is now made to the accompanying drawings, showing by way of illustration a preferred embodiment thereof, and in which:

FIG. 1 is a perspective view of an adjustable bed in accordance with the present disclosure, shown in a fully collapsed low profile position;

FIG. 2 is a side elevational view of the bed as seen in FIG. 1;

FIG. 4b is a partial side elevational view of a head-end of the bed as seen in FIG. 4a;

FIG. 4c is a partial side elevational view of a foot-end of the bed as seen in FIG. 4a;

FIG. 5 is a partial lower perspective view of the present bed shown in the fully elevated position;

FIG. 7 is an enlarged upper perspective view of a portion of the mattress platform of the adjustable bed;

FIG. 8 is a top plan view of a foot-end of the adjustable bed;

FIG. 9 is a perspective view of a main frame of the adjustable bed;

FIG. 10 is an enlarged side elevational view of the inside of the main frame of FIG. 9, showing the curvilinear tracks formed within the longitudinally extending beams of the main frame;

FIG. 11A is a side elevational view of an adjustable bed in accordance with an embodiment of the present disclosure;

FIG. 11B is a partial side elevational view of a head-end of the bed as seen in FIG. 11A; and FIG. 11C is a partial side elevational view of a foot-end of the bed as seen in FIG. 11A.

DETAILED DESCRIPTION

The adjustable bed as described herein provides a low-profile bed which is able to collapse down into a very low profile elevation while still providing a high load lift capacity. For example, the minimum vertical height between the ground and the mattress supporting surface in the low-profile elevation of the present adjustable bed is at least less than 9 inches, and may be less than 8.5 inches, while still providing a lift capacity of at least greater than 850 lbs, and preferably greater than 1000 lbs (such as between 1000 lbs and 2000 lbs, and more preferably between 1000 and 1600 lbs). In a particular embodiment of the present adjustable bed, the minimum vertical height in the low profile bed configuration is between 6 and 9 inches. In a more preferred embodiment, the minimum vertical height is between 8 and 8.5 inches, and may be approximately 8.25 inches. To date, all known low-profile beds sacrifice lift capacity to be able to collapse into such a small elevational envelope, or alternately permit such a high lift capacity but as a result are much larger and thus cannot collapse down into a sub-9 inch elevational envelope and thus would not be considered "low profile" as defined herein. The present adjustable bed, as will be described in detail below, is designed and constructed such as to enable both a maximum lift capacity of more than 1000 lbs while still having a minimum vertical height of less than 9 inches, and preferably between 8 and 8.5 inches, when fully collapsed into its low-profile configuration. Additionally, the present adjustable bed does this while still permitting a large vertical height adjustment range (ex: from 8 to over 30 inches) as well as a full range of both fore-aft tilt orientation of the main frame and angular adjustments between the articulated sections of the mattress supporting platforms. Additionally, the present bed includes a fixed frame base and permits the full range of vertical height adjustment without any longitudinal displacement of the bed during this travel.

Although the adjustable furniture article of the present invention will be generally described with respect to an articulated bed of the type used in hospitals and other medical applications, it is to be understood that the design and configuration of the present adjustable furniture article can be used for other applications, preferably although not necessary in a medical, dentistry or veterinary fields. For example, the presently described adjustable device can be applied to and used in an adjustable table or other platforms of the type, for example, used in surgical applications, for supporting large animals in veterinary applications and/or other vertically adjustable platforms/tables, as well as for an adjustable chair of the type used by dentists.

Figure 3A:
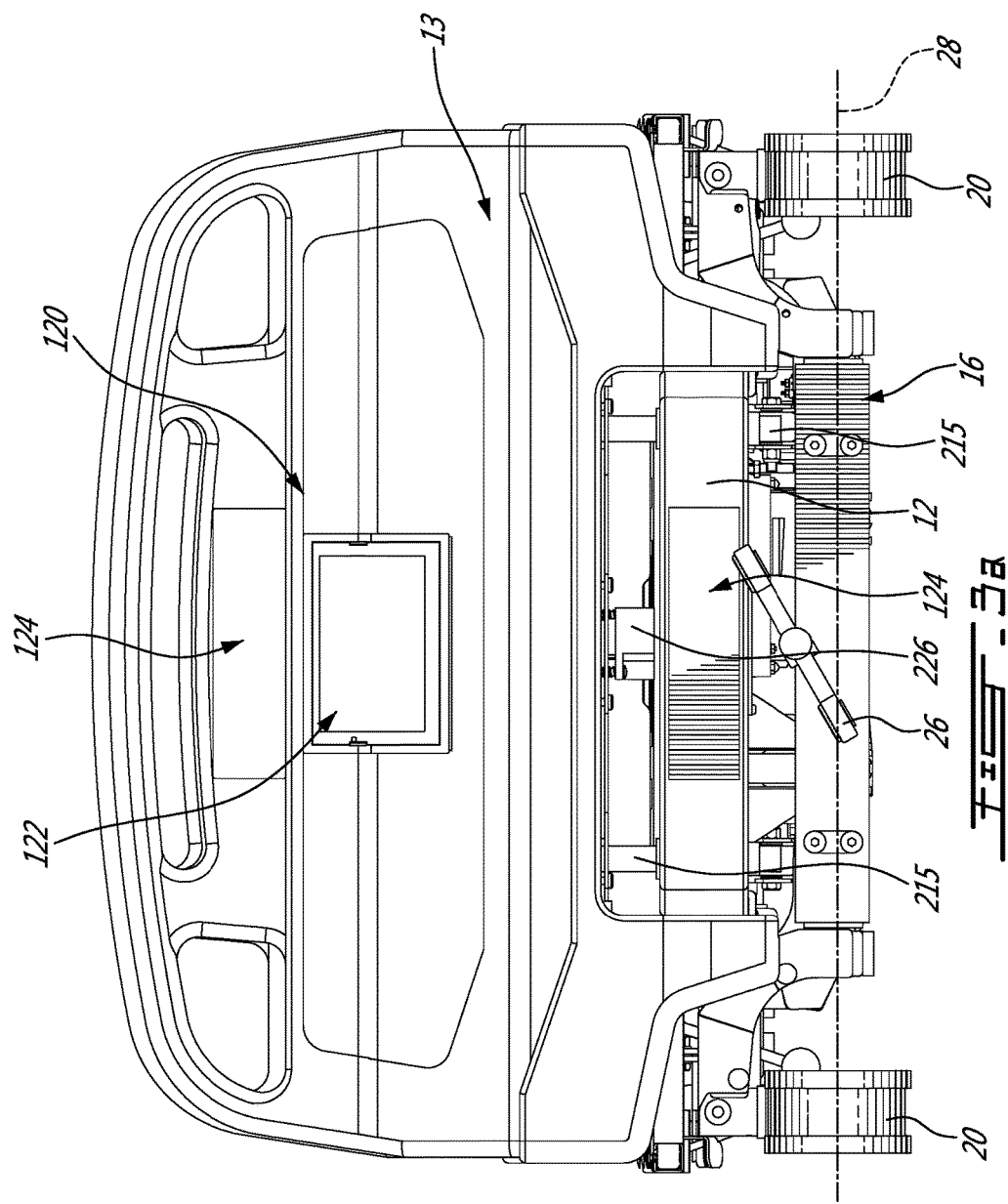
FIG. 3a is an end view of the bed as seen in FIG. 1.
Figure 3B:
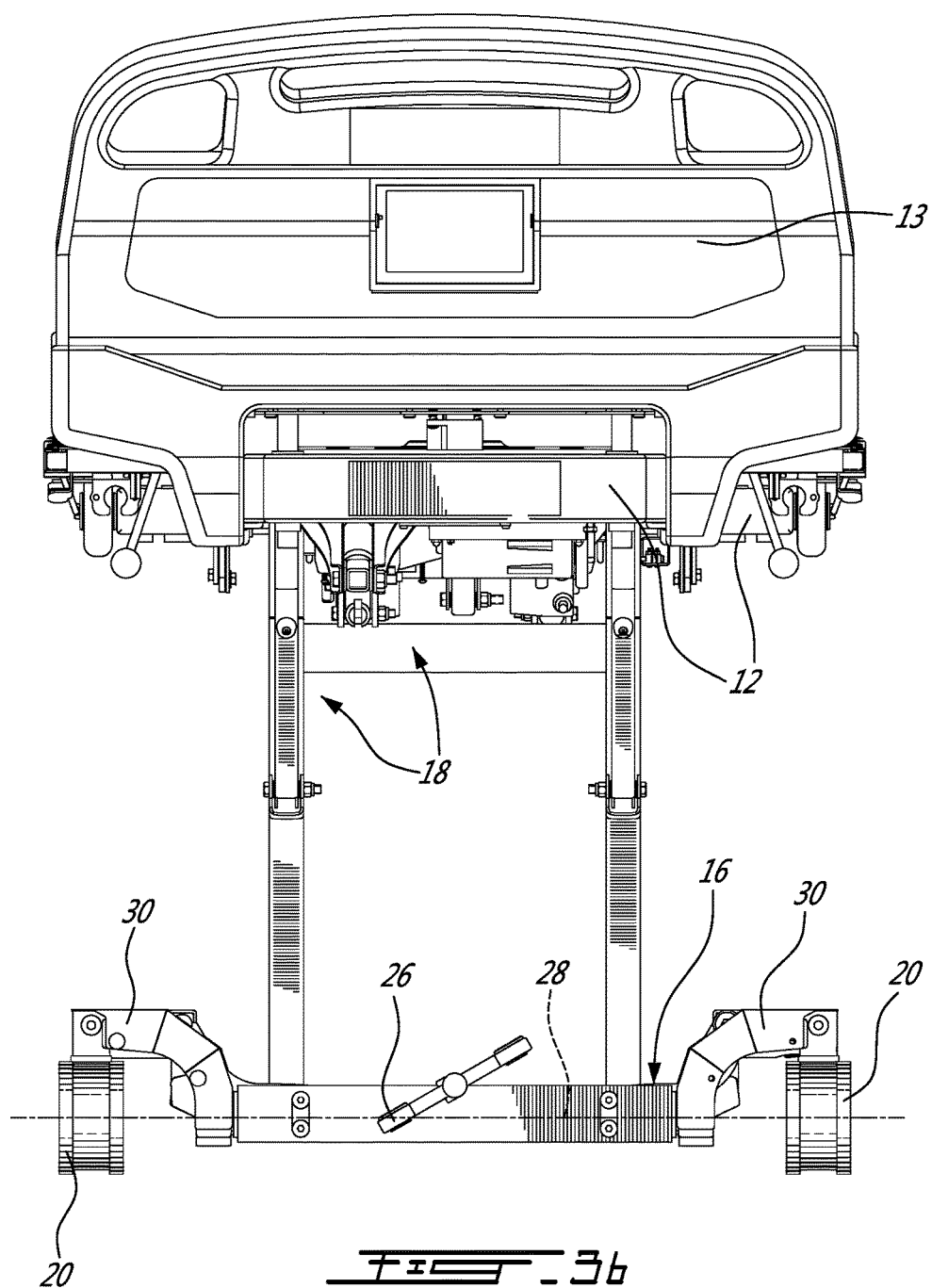
FIG. 3b is an end view of the present bed, shown in a fully elevated position.
Figure 4A:
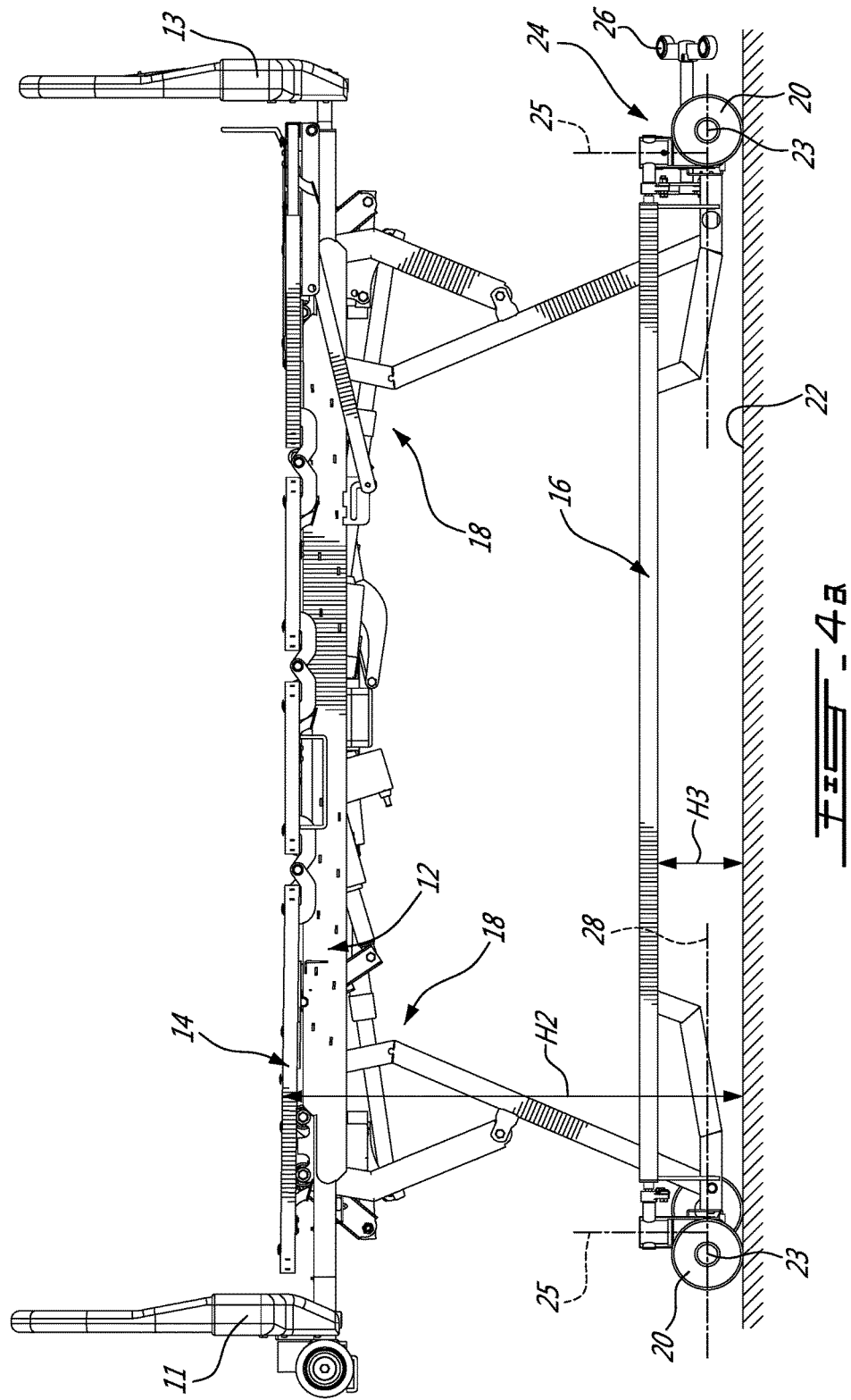
FIG. 4a is a side elevational view of the bed as seen in FIG. 3b.

Referring first to FIGS. 1-4a, the adjustable bed 10 includes a main frame 12 to which is mounted a mattress support platform 14. The generally rectangular bed 10 includes a headboard 11 engaged to a head end of the main frame 12 and a footboard 13 engaged to a foot end of the main frame. Preferably, although not necessarily, one or both of the headboard 11 and footboard 13 are removably engaged with the main frame 12, such they can be quickly and easily disconnected therefrom, such as by simply lifting it vertically upward. The main frame 12 is interconnected with a fixed frame base 16 by a lift mechanism 18. The lift mechanism 18 thus supporting the main frame 12 and is actuable to displace and position the main frame 12 between a fully collapsed position (as shown in FIGS. 1-2) and a fully elevated position (as shown in FIGS. 3b and 4a) relative to the fixed frame base 16. The fixed frame base 16 includes wheels 20, preferably casters, mounted thereto for displacement of the fixed frame base on a floor surface 22.

The main frame 12, the fixed base 16 and the lift mechanism 18 intermesh, without obstructing each other, and collapse into the low profile bed configuration as best seen in FIG. 2, when the main frame 12, and therefore the entire bed, is lowered down into in the fully collapsed position. As seen in FIG. 2, in this fully collapsed position, the main frame 12 and the components of the lift mechanism 18 actually fit into and below the tubular structure of the fixed base frame 16, such that the only additional height is caused by the vertical thickness of the tubes used to form the mattress supporting platform 14. When in this low-profile, fully collapsed position, the upper surface of the mattress platform 14, which is mounted to the main frame 12, is located at a minimum vertical height H1 above the floor surface 22. In at least one particular embodiment, this minimum vertical height H1 in the collapsed position is at most 9 inches, but may be 8 inches or less in a more preferred embodiment. Although the fully-elevated height H2 (see FIG. 4a) of the mattress platform 14 may vary, it one particular embodiment it is at least 30 inches, and thus the overall vertical elevation travel range is between 21-22 inches.

The adjustable bed 10 is a so-called "fixed base" bed, wherein the base frame 16 defines a tubular frame structure which at least partially lies in a plane 28 (see FIG. 4a) that remains substantially parallel to the floor surface 22, regardless of the vertical elevation of the main frame 12—i.e. regardless of whether the main frame is in a fully collapsed position (FIG. 2), a fully elevated position (FIG. 4a) or any elevation therebetween. The wheels 20 mounted to the fixed frame base 16 remain in fixed locations (while still being able to pivot and rotate, when required) on the outer periphery of the fixed frame base 16, preferably at the four corners of the rectangular shaped base frame, regardless of the vertical position of the main frame 12 relative to the fixed frame base 16. In other words, throughout the full vertical height travel of the main frame 12, and thus the mattress support platform 14 thereon, the wheels 20 remain substantially stationary relative to the fixed base frame 16 and thus substantially longitudinally stationary and level on the floor surface 22. This is not the case, for example with collapsible bed designs which use two pivoting legs having a wheel on the lower ends thereof, such as for example the above-mentioned U.S. Pat. No. 6,473,922 issued Nov. 5, 2002.

Further, another particular advantage enabled by the fixed frame base 16 is that because it remains level, i.e. substantially parallel to the ground surface 22, at all times, the load cells which are incorporated directly into the wheel assemblies on the fixed base can at all times accurately measure the weight of the patient on the bed. This is not always possible in prior art bed designs, wherein the bases of the bed frame upon which the wheels are mounted become tilted and can be disposed at any number of angles when the sleeping surface is raised or lowered. As such, in these prior art designs, accurate measurement of the patient's weight can only be accomplished at certain pre-defined positions of the sleeping surface, such as only at the fully elevated or fully collapsed positions for example. Because the fixed base frame 16 of the present bed 10 remains level at all times, regardless of the vertical position of the main frame 12 and the mattress support platform 14 thereon, the load cells in the wheels assemblies mounted on the base frame 16 can at all times, and at all vertical elevations of the platform, accurately measure the patient's weight. This can mean significant time and effort savings for the operator of the bed, such as a medical professional for example, as needless rising and lowering of the bed is not required simply to accurately measure the load imposed on the bed (i.e. the patient's weight).

As best seen in FIG. 4a, the wheels 20 mounted to the ends of the fixed base frame 16 are preferably caster assemblies which define a horizontal rotation axis 23 of the wheels as well as a vertical caster pivot axis 25, such that when the wheels are fully unlocked by a wheel locking mechanism 24 they can both roll about axes 23 and pivot around axes 25 such that the wheels will align themselves automatically with the direction of travel of the respective end of the bed. The wheel locking mechanism 24 enables individual wheels to be selectively locked, such than any one or more of the four wheel assemblies can be either partially locked (i.e. prevented from rolling about axis 23) or fully locked (i.e. prevented from both rolling about axis 23 and pivoting about axis 25). The wheel locking mechanism 24 is controlled by a single foot-actuated pedal 26, that is located at the foot end of fixed frame base 16 below the footboard 13. Accordingly, all wheels can be centrally locked and unlocked by a single break pedal 26, which is a significant improvement of most prior art bed designs whereby individual wheels must be separate lock and/or unlocked in tern. Further by positioning the foot-actuated pedal 26 of the wheel locking mechanism 24 at the foot end of the bed, rather than along a longitudinal side edge of the bed as is typical of prior art beds, this greatly simplifies the ability to manipulate and manoeuvre the bed from the foot end thereof, for example by grasping the footboard 13 to push, pull and/or steer the bed as may be require to displace it into a desired position on the floor surface.

As noted above, the fixed frame base 16 defines a plane 28 within which at least a portion of it lies and which remains substantially parallel to the floor surface 22 regardless of the vertical elevation position of the main frame 12 and mattress platform 14. As can be seen in both FIGS. 3a-3b, this plane 28 of the fixed frame base 16 is located approximately at or lower than the elevation as the horizontal rotation axis 23 of the wheels 20 of the caster assemblies. This is made possible due to the shape of the caster support arms 30, which as best seen in FIG. 3b, have an upward and outwardly curved shape, thereby enabling the lowest point on the fixed frame base 16 to be as close as possible to the ground surface 22 on which the wheels are resting. In other words, the shape of the caster supports arms 30 enable the lowest portion of the fixed base frame 16 to be dropped down within the vertical height defined by the diameter of the wheels themselves. Accordingly, when disposed in the fully collapsed position, the top surface of the main frame 12 is able to nearly vertically line up with the top of the caster support arms 30 of the wheel caster assemblies, resulting in a very compact package as seen in FIGS. 2 and 3a.

In a preferred embodiment, relatively large diameter wheels 20 are preferably used, as this generally improves the ease of displacement of the bed. As can be seen in the depicted embodiment (see FIG. 2), the wheels 20 mounted to the fixed base frame 16 may have a diameter that is more than half of the total minimum vertical height H1 of the bed in the low profile bed. In one possible embodiment, the wheels 20 have a diameter of approximately 5 inches, while the overall minimum vertical height of the mattress platform 14 above the ground surface 22 remains only 8-9 inches. Of course, other diameters and relative wheel size to minimum vertical height are also possible, and may vary depending on the application intended for the particular bed.

Another useful feature of the present bed 10 is that, despite its ability to collapse down into a very low profile size envelope as seen in FIG. 2, when the main frame 12 and mattress support platform 14 is elevated, as shown in FIG. 4a for example, there nevertheless remains a sufficiently large vertical clearance gap H3 beneath the longitudinally extending tubes of the fixed base frame 16, at least at in a longitudinally central region thereof, such as to permit access beneath the bed. This can be useful and/or required, for example such that legs or bases of rolling medical equipment can be slid beneath the bed 10. The vertical clearance gap H3 may be, in at least on particular embodiment, up to 6 inches. For a low-profile bed 10 having a minimum overall fully collapsed height of only 8-9 inches, a clearance gap of 6 inches beneath the fixed base frame is particularly large.

Figure 4B:
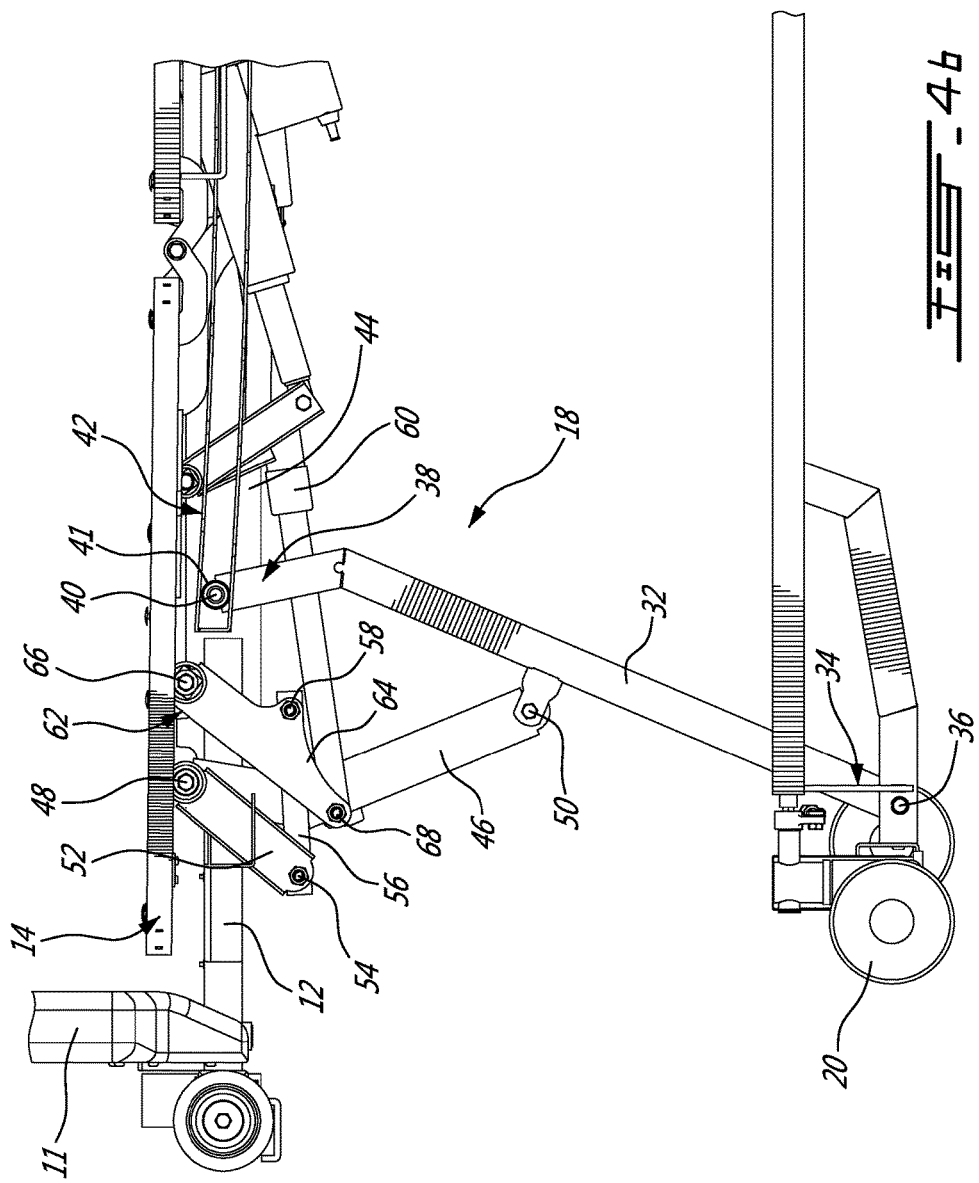

The lift mechanism 18 will now be described in greater detail, with particular reference to FIGS. 4b-5. As noted above, the lift mechanism 18 supports the main frame 12 and is actuable to displace and position the main frame 12 in the desired vertical position, permitting the main frame 12 and thus the mattress support platform 14 mounted thereto to be displaced between the fully collapsed position and the fully elevated position, relative to the fixed frame base 16. Referring particularly to FIG. 4b, the lift mechanism 18 includes at least a first leg member 32 (in this case the head-end leg) having a first, lower, end 34 pivotally connected with the fixed frame base 16 at a fixed lower pivot 36 and a second, upper, end 38 pivotally connected with the main frame 12 at a movable upper pivot 40. The leg member 32 is bent at a point proximate the second end 38 thereof, such as to enable the fully collapsed position (as seen in FIG. 2, for example). The movable upper pivot 40 may comprise a roller or slider 41 which is constrained for displacement within a curvilinear track 42 that is fixed to one of the longitudinally extending tubes 44 of the main frame 12 (see FIGS. 9 and 10). In a preferred, but not essential embodiment, the curvilinear tracks 42 are in fact formed directly within the body of the longitudinally extending tubes 44 of the main frame, as opposed to being guide tracks welded to the outer surface of the tubes 44, and may be formed therein by any suitable method such as by laser cutting the predetermined curved slot in the inner wall of the longitudinally extending tubes 44.

As best seen in FIGS. 9 and 10, the curved travel axis for the movable upper pivot points of the leg members within the curvilinear tracks 42 declines towards a longitudinal center of the main frame 12, such that they extend from a high point at a longitudinal outer end of the curvilinear track 42 to a low point at a longitudinally inner end of the curvilinear track. As seen in FIG. 10, the two curvilinear tracks 42 (i.e. one for the movable upper pivot of the head-end leg member and the other for the movable upper pivot of the foot-end leg member) in each of the longitudinally extending tubes 44 of the main frame 12 are mirror images of each other relative to a longitudinal central midpoint.

Accordingly, the movable upper pivot 40 of the head-end leg member 32 is translatable within this curvilinear track 42, when the leg is pivoted about its fixed lower pivot point 36. The movable upper pivot 40 is therefore displaced along a curved axis defined by the curvilinear track 42, the curved axis thus having both vertical and longitudinal components. Displacement of the movable upper pivot 40 of the leg member 32 within the curvilinear track 42 constrains pivoting motion of the leg member 32. The lift mechanism 18 and the geometry of the components thereof accordingly permits the main frame to remain substantially horizontal throughout the full movement thereof between the fully collapsed position and the fully elevated position, and this without causing any longitudinal displacement of the main frame and mattress platform. The curved translational movement of the movable upper pivot 40 of the leg member 32, and the similar movement of the upper pivot of the similar and corresponding foot-end leg member, thus help to control the movement of the main frame and mattress platform assembly through the full vertical travel thereof, without causing any longitudinal displacement relative to the fixed base frame. In other words, the vertically moving main frame remains directly centered above the fixed base frame at all times through its vertical travel, without any unwanted longitudinal displacement of the bed, due at least in part to the curvilinear track 42 which constrains the movable upper pivots 40 to be displaced along the curve axis. This curved travel path constrained by the curvilinear tracks 42 also helps to provide initial assistance, or rather helps to reduce the initial resistance to upward displacement, when the main frame is first actuated by the lift mechanism 18 to move away from the fully collapsed low profile position.

Referring particularly to FIG. 4b, the lift mechanism 18 further includes at least one stabilizer link 46 for each leg member, at least one actuator 60 and a force-multiplying actuating linkage 62 interconnecting the actuator 60 and the stabilizer link 46. The actuator has a first end (in this case a longitudinally central end) engaged to the main frame 12 and a second free end pivotally connected with the force multiplying actuating linkage 62.

The force multiplying actuating linkage 62 includes a driving link 64 and an intermediate link 56, the driving link 64 having an upper end pivotally mounted to the main frame at first rocker pivot 66 and a lower free end, which pivots about the first rocker pivot 66, pivotally connected to the second end of the actuator 60 at the actuator pivot point 68. The intermediate link 56 has a first end pivotally connected to the driving link 64 at a point on the driving link 64 between the upper and lower ends thereof, and an opposed second end of the intermediate link 56 being pivotally engaged with the stabilizer link 46, and more particularly with the torque arm 52 thereof as noted below.

The stabilizer link 46 having an upper end pivotally connected with the main frame 12 at a second rocker pivot 48 and a lower end pivotally connected with the leg member at an intermediate pivot point 50 disposed on the leg member between the first end 34 and second end 38 thereof, but not necessarily at the midpoint thereof. Actuation of the stabilizer link 32 by rotation about its rocker pivot 48 thus causes the leg member 32 to be displaced. The stabilizer link 46 includes a torque arm 52 which extends from the fixed rocker pivot point 48 thereof and thus defines a remote end disposed a distance away from the upper end of the stabilizer link but being fastened thereto such that rotation of the torque arm 52 causes a corresponding rotation of the stabilizer link 46. The second rocker pivot point 48 may for example be formed by a horizontal tube to which is fastened, such as by welding, both the upper end of the stabilizer link 46 and the upper end of the torque arm 52. The remote end of the torque arm is pivotally connected at torque arm pivot 54 with the intermediate link 56. Particularly, the intermediate link 56 has one end pivotally connected with the remote end of the torque arm 52 and the opposed end pivotally connected at pivot joint 58, the opposed second end of the intermediate link being pivotally connected with the remote end of the torque arm.

It is of note that both the first and second rocker pivots 66 and 48 define parallel and spaced apart rotation axes about which the driving link 64 and the torque arm 52 of the stabilizer link 46 rotate.

This force multiplying actuating linkage 62 of the lift mechanism 18 generates a force multiplication effect, such that a relative large load (at least greater than 850 lbs, and preferably greater than 1000 lbs) can be raised by the lift mechanism 18, even from the very low fully collapsed position, without requiring either a large capacity actuator or extremely long and massive torque levers as is typically required in prior art designs. Further, another advantage of the lift mechanism 18, and thus of the entire bed 10, is that it provides a very good lift capacity to weight ratio, or "force" to weight ratio, in that a bed which itself weighs less than 500 lbs is readily capable of lifting loads of twice as much, and this with actuators of a relatively modest force output (ex: 10,000 N). The force multiplying actuating linkage 62 of the lift mechanism 18 enables high force and thus torque to be generated from a very compact system. Long torque bars, which are sometimes used in prior art beds specifically designed for obese patients and other high lift load uses because they enable more torque and thus lifting force to be generated, cannot be accommodated in a low-profile design such as that of the present bed 10 where the minimum vertical height available is less than 9 inches, as such long torque bars simply cannot fit within the small (ex: 4-8 inch) space envelop available into which all components need to fit when the bed is lowered into a fully collapsed low-profile position.

The actuators 60 of the present lift mechanism 18 may have a maximum force capacity of 10,000 N, for example, however in tests conducted only 7,000 N were found to be required to raise a load of over 1000 lbs. In fact, much higher maximum load capacities (ex: greater than 1550 lbs) were found to be possible using the lift mechanism 18 of the present bed 10.

Referring back to FIG. 4c, the lift mechanism 18 which actuates the other leg member, namely the foot-end leg 70 is very similar to that described above with respect to the head-end leg 32. Accordingly, similar reference numbers have been used in FIG. 4c for corresponding parts in those portions of the lift mechanism 18, actuating assembly and force multiplying linkage 62 which are provided to actuate the foot-end leg member 70. The foot-end portion of the lift mechanism 18 differs only slightly from that of the head-end portion shown in FIG. 4c, in that the lower end 34 of the foot-end leg member 70 includes a moving pivot joint 63 with the fixed base frame 16, rather than a fixed pivot point as per the pivot 36 between the lower end of the head-end leg 32 and the fixed base frame. The moving pivot 63 of the foot-end leg member 70 is therefore displaceable within a longitudinally extending slot formed in a tube of the fixed base frame 16. Accordingly, both the upper and lower pivots of the foot-end leg 70 are sliding pivot joints, i.e. neither is a fixed pivot joint. As such, the foot-end leg 70 rotates, as the bed is raised and lowered, about a displacing virtual pivot point. This sliding pivot joint 63 between the lower end 34 of the foot-end leg 70 and the fixed base frame 16 helps to permits the main frame 12 and mattress platform 14 to be inclined about a transverse inclination axis (such as to incline the bed for example if it becomes necessary to raise or lower the patients feet with respect to their head, or vice versa), without causing any longitudinal displacement of the main frame 12 and platform 14 subassembly.

Figure 6:
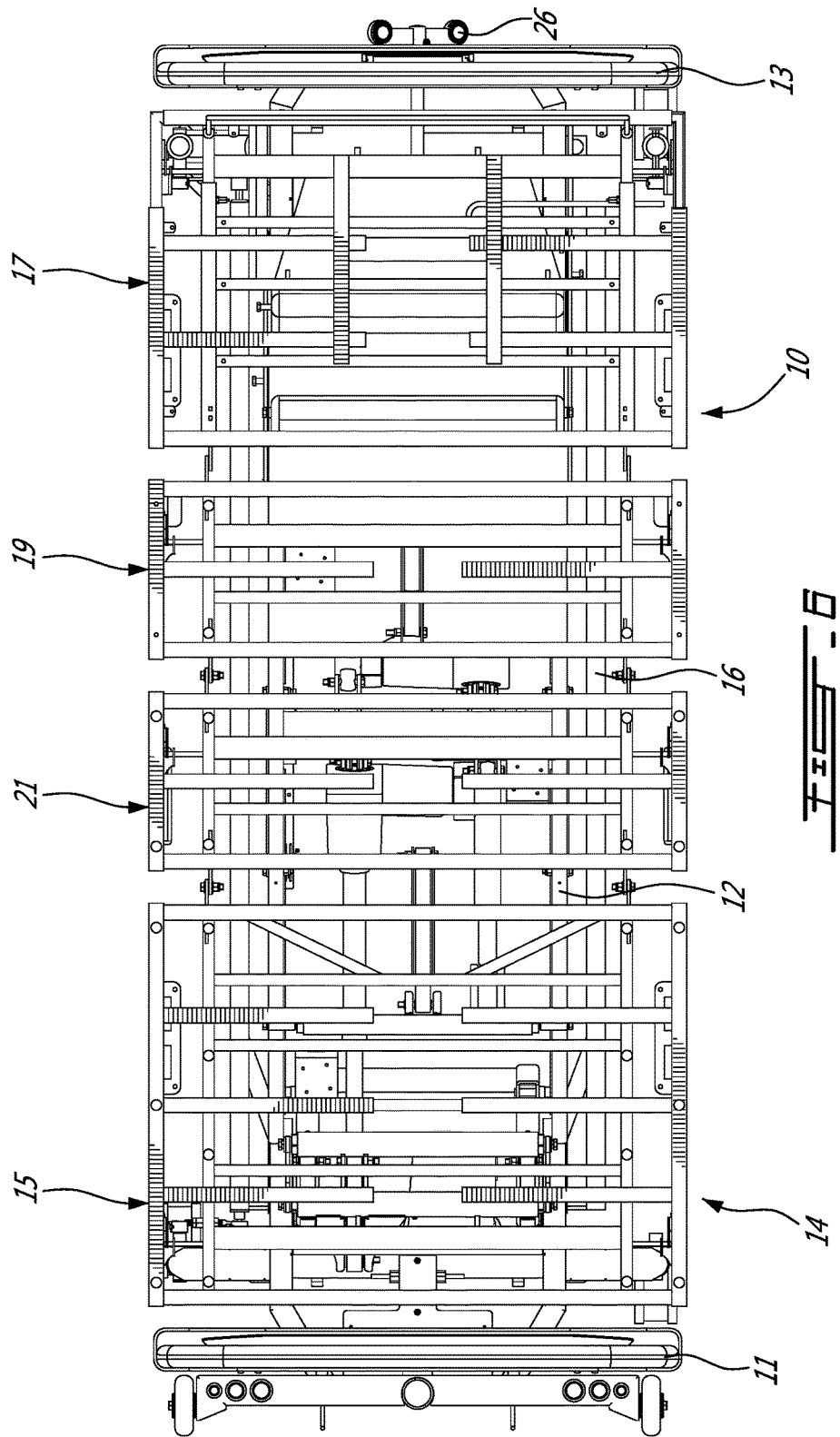
FIG. 6 is a top plan view of the bed as seen in FIG. 1.

Referring now back to FIG. 1 and to FIG. 6, the mattress support platform 14 mounted on top of the main frame 12 may include at least two separate articulated platform sections, including a head portion 15 and a foot portion 17, which are interconnected and articulated relative to each other. Each of the head portion 15 and the foot portion 17 of the mattress support platform 14 is actuated by an independent actuator, such as to such permit adjustment of the relative angle therebetween from between 0 and 90 degrees. In the depicted embodiment, a third articulated platform portion, namely a knee support 19, and a fourth articulated platform portion, namely the lower back support portion 21, are also provided and are similarly articulated with the next adjacent platform section and are displaced as required, either in conjunction with the head and foot portions 15, 17 or independently therefrom.

An actuator is provided for displacing each of the foot and head portions of the platform, and each is individually controlled by a control box. In at least one embodiment of the bed, two separate control boxes are provided, one for the foot and one for the head half of the bed. Each of these control boxes controls two separate actuators, namely one being the vertical adjustment actuators 60 for operating the lift mechanism 18 and one for adjusting the inclination angle of the foot or head portions 17, 15 of the mattress support platform 14.

Figure 4C:
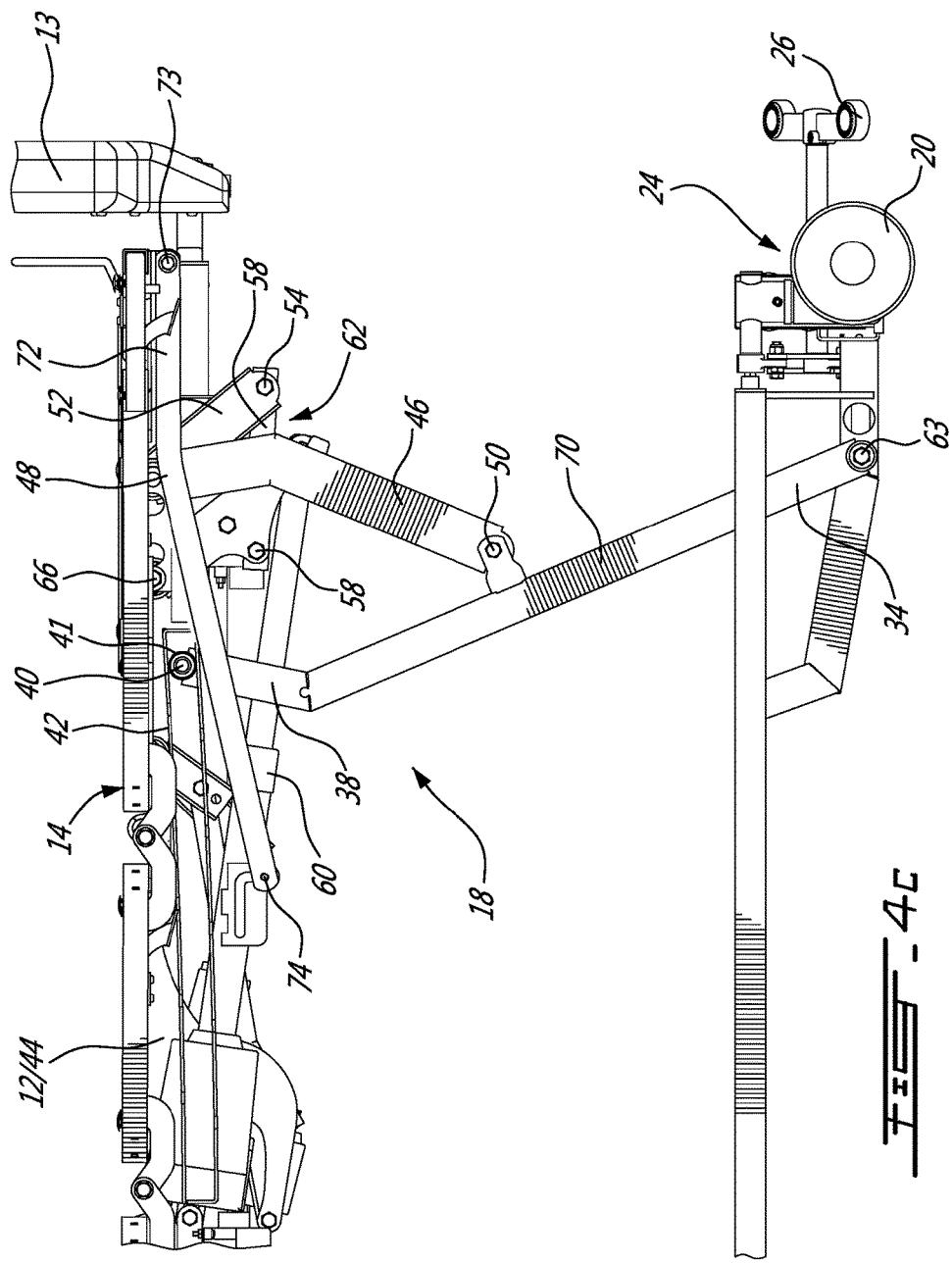

With particular reference to the adjustment of the foot portion 17 of the mattress support platform 14, as best seen in FIG. 4c, a linkage bar 72 is pivotally connected at a fixed pivot joint 73 with an end of the foot portion 17 of the platform 14 and has a moving pivot joint 74 at the opposite end of the linkage bar 72 which is slidingly received within an L-shaped slot formed within a bracket mounted on the main frame 12. This linkage bar 72 and the sliding pivot joint 74 accordingly permits the foot angle (i.e. the relative angle between the foot portion 17 of the platform 14 and the forward knee supporting portion 19) to be adjusted, such as by actuating the dedicated actuator which controls the inclination angle of foot platform portion 17, regardless of the vertical position of the entire main frame 12 (i.e. the vertical position of the bed) and additionally without causing any unwanted longitudinal displacement of the platform 14.

Referring now to FIGS. 7-8, in at least one embodiment of the bed 10, the platform 14 enables both lateral and longitudinal adjustment. More particularly, if it becomes necessary or desirable to widen the overall transverse width of the platform 14, such as to accommodate a large and/or heavier patient for example, the platform 14 is provided with quick-release type adjustment mechanism to quickly and easily modify both the width and/or length of the platform 14, and this while providing fully supported corners on each end of the platform. As seen in FIG. 7, the mattress platform includes at least one quick-release adjustment mechanism 80 which enables the width and/or length of the platform to be independently varied by sliding a displaceable outer edge of the mattress platform to be extended relative to a fixed central portion of the mattress platform while still providing full support at the corners of the rectangular mattress platform. The quick-release width adjustment mechanism 80 includes generally an actuating lever 81 which acts to rotate a bar 82 which extends laterally within at least a horizontal hollow tube 87 of the fixed mattress platform portion relative to which an outer longitudinal tube 86 of the displaceable outer edge is displaceable. The bar 82 has an L-shaped end 83 thereof which engages corresponding notches 84 defined in a slot 85 formed in the tube wall. This slot 85 is cut out of the side wall 91 of the platform tube 87, for example by laser cutting. Accordingly, the bar 82 translates within the tube 87 and the L-shaped end 83 is able to slide within the cut-out slot 85 and engage the notches 84, all without interfering with the mattress or the various height and position adjustment mechanisms, such that when the L-shaped end 83 is disposed in the notches 84 relative displacement between the displaceable outer edge 86 and the fixed mattress platform portion (ex: tube 87) is prevented. This mechanism permits the outer longitudinal tube 86, which forms the outer lateral edge of this particular portion (in this case the knee support portion 19) of the platform 14, to be quickly and easily (i.e. without requiring any tools, for example) laterally extended or retracted as needed, when the actuating lever 81 is deployed to thereby free the L-shaped bar end 83 from its engaging notches 84.

Similarly, as best seen in FIG. 8, the platform 14 includes corner adjustment mechanisms 92 which enable integrated easy adjustment of both the length and width of the full platform at the corners thereof, also without requiring and tools and time consuming modifications. The corners of the platform 14 are formed such that the longitudinal tubes 88 of the platform 14 have a smaller corner tube member 89 telescopically received therein, such as to permit longitudinal adjustment of the length of the foot portion 17 of the platform 14. Additionally, the smaller corner tube subassembly 89 is also telescopically mated with a lateral end tube 90, such that the lateral width of the same foot portion 17 of the platform 14 can be adjusted and varied as required. A similar adjustment mechanism may be provided on the head portion 15 of the platform. Accordingly, these platform adjustment systems permit the width and/or the length of each platform section to be quickly and easily modified as required, without having to sacrifice a corner region of the platform which does not provide any support. In this regard, known prior art platforms which do offer any adjustment, always do so at the sacrifices of a fully supported corner of the mattress because the void in the corner region is always left when separate (i.e. not integrated, as per the above-described corner adjustment mechanism 92) length and width modifications are possible.

Referring now back to FIGS. 1 and 3a, the footboard 12 of the bed 10 may include one or more control panels 120 thereon, such as an LCD touch-screen 122 and/or a more traditional control panel 124 having a number of push-buttons thereon. As seen, both the footboard 13 and the foot-end of the main frame 12 may have such a push-button control panel 124, such that if/when the footboard is disconnected from the main frame and removed, control of the adjustable bed 10 remains possible. As noted above, at least the footboard 13 is removably engaged with the main frame 12, such as by posts 215 which protrude therefrom and are matingly received within corresponding holes formed in the foot-end of the main frame. An electrical quick-connect junction 226 is used to electrically interconnect the footboard 13 with electronics and power signals from the main frame, such that when the footboard 13 is slid down into engagement with the main frame using the alignment posts 215, the mating halves of the quick-connect junction 226 plug into one another thereby providing power to the control panels on the headboard and permitting electrical communication between the control system of the main frame and the panels of the electronics of the footboard.

The bed 10 thus includes an electrical control system, which may be operated for example by the touch-screen 122 on the footboard 13, and which includes an on-board computer that is programmed such as to enable all operations of the bed to be controlled from this point. For example, as mentioned above, the caster wheel assemblies 20 may be provided with load cells, such that they are able to measure the load applied on the bed (i.e. to measure the weight of the patient) when on the bed. The control system is accordingly able to measure and display on the touch-screen 122, the weight of the patient in real time, and this regardless of the position of the bed (ex: fully collapsed, fully elevated and/or at any angular position of the mattress support platform). Accordingly, the control system is programmed such as to provide a bed-exit alarm feature, whereby when this feature is activated, an alarm will sound (which may include an audible alarm as well as a visual warning on the screen 122) when a patient gets off the bed (i.e. the signal sent from the load cells in the wheels 20 to the control system indicates that substantially all load on the bed has been suddenly removed). This feature can be activated and de-activated as needed, for example by the healthcare professional operating the system via the touch-screen 122.

Additionally, because the control system enables the patient's weight to be measured in real time, and further that the on-board computer includes a memory which permits the patient's measured weight to be continuously saved and recorded over a given period of time, the software programmed into the on-board computer permits the touch-screen 122 to display, for example, a numerical and/or graphical representation of any change in the patient's weight over time. This can be particularly useful, for example, in cases when a healthcare professional wishes to monitor a patient's weight in order to detect any significant changes thereto which could be indicative of either an improvement or a deterioration of the patient's medical condition. When graphically illustrated, such as on a line graph whereby the patient's measured weight is shown in a vertical axis and time is shown on a horizontal axis, the touch-screen 122 permits the user to touch at any point in time on the horizontal axis to visually reveal the exact measured weight of the patient at that specific point in time. A horizontal axis slider may also be displayed, such that touching and then horizontally displacing the slider will move forward and backward in time, the measured weight of the patient at any point in time being depicted. For example, if the control system has been set, as controlled by the touch-screen 122, such as to measure the patient's weight over a period of 24 hours, at any time (either during this 24 hours or at a later date/time) the user is able to touch the depicted graph at a desired point in recorded time (ex: 6 hours ago) and the touch-screen 122 will show the exact numerical value of the patient's weight as measured at that specific point in time.

Another feature provided by the control system of the bed 10, and thus which can be displayed on the touch-screen 122, is the graphical representation of the angles of each of the displaceable portions of the adjustable bed, such as the vertical height of the main frame 12 and/or the relative angular positions of the articulated portions of the mattress support platform 14. Additionally, the control system permits the relative angles of these portions of the mattress support platform 14 to be adjusted as required, either manually or automatically such as to maintain a desired relative angle throughout a full range of motion of the bed (both vertical height adjustment and fore-aft longitudinal tilt angle). For example, if the head portion 15 of the mattress support platform 14 is disposed at a 45 degree angle relative to the horizontal, and the knee and foot support portions 19 and 17 of the platform are disposed having a relative angle of 70 degrees therebetween, then as the entire main frame 12 is inclined relative to the horizontal (and thus relative to the fixed base frame 16) about a transversely extending fore-aft inclination axis, the control system can adjust the relative angles of the platform segments as necessary to maintain the same angles and/or a constant relative position, regardless of the inclination angle of the entire main frame 12. The actual angular positions of the platform segments are depicted on the touch screen 122, for example in a graphical representation (line representing each segment depicted angled relative to each other) and/or a numerical representation (exact angles relative to a common reference or relative to each next segment).

Referring now to FIGS. 11A to 11C, an adjustable bed 110 in accordance with another embodiment is shown, and includes a main frame 112 having a mattress support platform 114, and a lift mechanism 118 for the adjustable bed 110 that is incorporated within the fixed frame base 116, rather than the mattress support platform 114.

More particularly, referring to FIGS. 11B and 11C. The lift mechanism 118 of the adjustable bed 110 includes at least one stabilizer link 146 for each leg member 132, at least one actuator 160 and a force-multiplying actuating linkage 162 interconnecting the actuator 160 and the stabilizer link 146. The actuator 160 has a first end engaged to the fixed frame base 116 and a second free end pivotally connected with the force multiplying actuating linkage 162.

The force multiplying actuating linkage 162 includes a driving link 164 and an intermediate link 156. The driving link 164 has a first end pivotally mounted to the fixed frame base 116 at a first rocker pivot 166 and a second end, which pivots about the first rocker pivot 166, pivotally connected to the second end of the actuator 160 at the actuator pivot point 168. The intermediate link 156 has a first end pivotally connected to the driving link 164 at a point on the driving link 164 between its first and second ends. In the depicted embodiment, an opposed second end of the intermediate link 156 is pivotally engaged with the stabilizer link 146, and more particularly, with the torque arm 152. In an alternate embodiment, the second end of the intermediate link 156 is pivotally engaged with one of the leg members 132.

The stabilizer link 146 has a first end pivotally connected with the fixed frame base 116 at a second rocker pivot 148 and a second end pivotally connected with the leg member 132 at an intermediate pivot point 150 disposed on the leg member 132 between the its two opposed ends, but not necessarily at the midpoint thereof. Actuation of the stabilizer link 146 by rotation about its rocker pivot 148 thus causes the leg member 132 to be displaced. The stabilizer link 146 includes the torque arm 152 in the depicted embodiment. The torque arm 152 has a first end pivotally connected with the fixed frame base 116 at the second rocker pivot 148, and extends from the fixed frame base 116 and thus defines a remote end disposed a distance away from the first end of the stabilizer link 146 but being fastened thereto such that rotation of the torque arm 152 causes a corresponding rotation of the stabilizer link 146. The second rocker pivot 148 may for example be formed by a horizontal tube which is fastened, such as by welding, to both the first end of the stabilizer link 146 and the first end of the torque arm 152. The remote end of the torque arm 152 is pivotally connected at torque arm pivot 154 with the intermediate link 156. Particularly, the intermediate link 156 has one end pivotally connected with the remote end of the torque arm 152 and the opposed end pivotally connected at pivot joint 158. The opposed second end of the intermediate link 156 is pivotally connected with the remote end of the torque arm 152.

It is of note that both the first and second rocker pivots 166 and 148 define parallel and spaced apart rotation axes about which the driving link 164 and the torque arm 152 of the stabilizer link 146 rotate.

Referring to FIGS. 11B and 11C, the lower end 34 of each leg member 132 is pivotally connected with the fixed frame base 116 at a movable lower pivot 136. The movable pivot 136 may comprise a roller or slider 141 which is constrained for displacement within a track 142 of the fixed frame base 116. The track 142 may be curvilinear or linear. In either case, the track 142 defines a travel axis for the movable pivots 136 of the leg members 132 within the tracks 142. In the depicted embodiment, this travel axis defined by the track 142 rises towards a longitudinal center of the fixed frame base 116, such that it extends from a low point at a longitudinal outer end of the track 142 to a high point at a longitudinally inner end of the track 142. In an alternate embodiment, the track 142 is not inclined, such that is oriented substantially horizontally and parallel to the floor surface. In the case of a curvilinear track 142, both the track and the travel axis defined thereby curve between the low point at the longitudinal outer end of the track to the high point at the longitudinally inner end of the track. This curve may define a gradual, substantially constant radius.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. An adjustable bed, comprising:
a mattress support platform;
a fixed frame base having wheels for displacement of the adjustable bed on a floor surface, the fixed frame base at least partially lying in a plane substantially parallel to the floor surface, and the wheels remaining in fixed locations on the fixed frame base regardless of a vertical position of the mattress support platform relative to the fixed frame base; and
a lift mechanism interconnecting the mattress support platform and the fixed frame base, the lift mechanism being actuable to displace the mattress support platform between a fully collapsed position and a fully elevated position, the lift mechanism including:
two or more leg members each having a first end pivotally connected with the fixed frame base at a first pivot and a second end pivotally connected with the mattress support platform at a second pivot; and
an actuating assembly including at least one actuator having a force multiplying actuating linkage interconnecting the actuator and the fixed frame base, the actuator having a first end and a second end, the force multiplying actuating linkage including a driving link and an intermediate link, the driving link having a first end pivotally mounted to the fixed frame base and a second end pivotally connected to the second end of the actuator, and the intermediate link having a first end pivotally connected to the driving link between the first and second ends of the driving link, an opposed second end of the intermediate link being pivotally engaged with one of the leg members and a stabilizing link, the stabilizing link interconnecting one of the leg members and the fixed frame base.

2. The adjustable bed as defined in claim 1, wherein the stabilizing link has a first end pivotally connected with the fixed frame base, and a second end pivotally connected with said leg member at an intermediate pivot point disposed on the leg member between the first and second ends of the leg member.

3. The adjustable bed as defined in claim 2, wherein the opposed second end of the intermediate link is pivotally engaged with the stabilizing link.

4. The adjustable bed as defined in claim 2, wherein the stabilizer link includes a torque arm having a remote end disposed a distance away from the first end of the stabilizer link, the opposed second end of the intermediate link being pivotally connected with the remote end of the torque arm.

5. The adjustable bed as defined in claim 1, wherein one of the first pivot and the second pivot of each said leg member is translatable within a track to define a movable leg pivot, the movable leg pivot of each said leg member displacing along an axis defined by the track and having vertical and longitudinal components, the axis rising towards a longitudinal center of the fixed frame base, extending from a low point at a longitudinal outer end of the track to a high point at a longitudinally inner end of the track.

6. The adjustable bed as defined in claim 5, wherein the track is curvilinear and the axis defined by the curvilinear track is curved.

7. The adjustable bed as defined in claim 5, wherein said one of the mattress support platform and the fixed frame base includes one or more longitudinally extending, transversely spaced apart, beams, the track being formed within at least one of the longitudinally extending beams.

8. The adjustable bed as defined in claim 5, wherein displacement of said first or second pivot of the leg members within the track constrains pivoting motion of the leg members such that the main mattress support platform remains substantially horizontal throughout the full movement thereof between the fully collapsed position and the fully elevated position.

9. The adjustable bed as defined in claim 1, wherein the lift mechanism is actuable to displace the mattress support platform between the fully collapsed position and the fully elevated position relative to the fixed frame base without any longitudinal displacement of the adjustable bed on the floor surface.

10. The adjustable bed as defined in claim 1, wherein the mattress support platform and the lift mechanism collapse into a low profile bed configuration in the fully collapsed position, the mattress support platform being located at a minimum vertical height of between 6 and 9 inches above the floor surface in said low profile bed configuration.

11. The adjustable bed as defined in claim 10, wherein the wheels have a diameter that is more than half of the minimum vertical height in said low profile bed configuration.

12. The adjustable bed as defined in claim 1, wherein the lift mechanism generates in operation a lift force providing a maximum load capacity of greater than 850 lbs.

13. The adjustable bed as defined in claim 12, wherein the maximum load capacity is between 1000 and 1600 lbs.

14. The adjustable bed as defined in claim 1, wherein the fixed frame base defines a vertical clearance gap beneath longitudinally extending tubes of the fixed frame base and the floor surface, the clearance gap being up to 6 inches in at least a longitudinally central region of the fixed frame base.

15. The adjustable bed as defined in claim 1, wherein the plane of the fixed frame base is located at a vertical elevation equal to or lower than a rotation axis of the wheels mounted to the fixed frame base.

16. The adjustable bed as defined in claim 1, wherein the leg members include a head-end leg and a foot-end leg, the first pivot point between the first end of one of the head-end and foot-end legs and the fixed frame base being fixed, and the first pivot point between the first end of the other of the head-end and foot-end legs being displaceable within a longitudinally extending slot, such as to permit inclination of the mattress support platform about a transverse axis without causing any longitudinal displacement of the bed.

17. The adjustable bed as defined in claim 1, wherein the wheels are selectively lockable by a wheel locking mechanism actuated by a foot-actuated pedal such as to prevent, when actuated, at least one of rotation about a horizontal wheel rotation axis and pivoting about a vertical caster pivot axis, and wherein the foot-actuated pedal is disposed at a foot end of the bed.

18. The adjustable bed as defined in claim 17, wherein the foot-actuated pedal permits any individual one or more of the wheels to be locked.

19. The adjustable bed as defined in claim 1, wherein the mattress support platform includes at least one quick-release adjustment mechanism which enables at least one of the width and length of the mattress support platform to be independently varied by sliding a displaceable outer edge of the mattress support platform to be extended relative to a fixed central portion of the mattress support platform while still providing full support at the corners of the rectangular mattress support platform, the quick-release adjustment mechanism including an actuating lever which rotates, when actuated, a bar extending laterally within at least a hollow tube of the fixed mattress support platform, the bar having an L-shaped end which engages corresponding notches defined in a slot disposed in a side wall of the hollow tube, such that when the L-shaped end is disposed in the notches relative displacement between the displaceable outer edge and the fixed mattress support platform portion is prevented.

20. The adjustable bed as defined in claim 19, wherein the slot is cut out of the side wall of the hollow tube.

* * * * *